US012478537B2

(12) United States Patent
Hynes et al.

(10) Patent No.: US 12,478,537 B2
(45) Date of Patent: Nov. 25, 2025

(54) FRAME AND PATIENT SUPPORT, AND SURGICAL METHODS USING SAME

(71) Applicant: EMPLASE Medical Technologies, LLC, Cordova, TN (US)

(72) Inventors: Richard A. Hynes, Melbourne, FL (US); Matthew M. Morrison, Cordova, TN (US); Roger P. Jackson, Prairie Village, KS (US)

(73) Assignee: Emplase Medical Technologies, LLC, Cordova, TN (US)

( * ) Notice: Subject to any disclaimer, the term of this patent is extended or adjusted under 35 U.S.C. 154(b) by 0 days.

(21) Appl. No.: 18/916,261

(22) Filed: Oct. 15, 2024

(65) Prior Publication Data

US 2025/0120865 A1 Apr. 17, 2025

Related U.S. Application Data

(60) Provisional application No. 63/544,430, filed on Oct. 16, 2023.

(51) Int. Cl.

| | |
|---|---|
| ***A61H 1/02*** | (2006.01) |
| ***A61B 17/70*** | (2006.01) |
| ***A61G 13/00*** | (2006.01) |
| ***A61G 13/12*** | (2006.01) |

(52) U.S. Cl.
CPC ......... *A61H 1/0292* (2013.01); *A61B 17/705* (2013.01); *A61G 13/0054* (2016.11); *A61G 13/123* (2013.01); *A61G 13/126* (2013.01); *A61G 13/129* (2013.01)

(58) Field of Classification Search
CPC .............. A61G 13/0054; A61G 13/123; A61G 13/126; A61G 13/129
See application file for complete search history.

(56) References Cited

U.S. PATENT DOCUMENTS

| | | | |
|---|---|---|---|
| 5,564,662 | A | 10/1996 | Lussi et al. |
| 7,152,261 | B2 | 12/2006 | Jackson |
| 7,290,302 | B2 | 11/2007 | Sharps |
| 7,343,645 | B2 | 3/2008 | Li |
| 7,565,708 | B2 | 7/2009 | Jackson |
| 8,060,960 | B2 | 11/2011 | Jackson |
| 8,381,331 | B2 | 2/2013 | Sharps et al. |
| 8,584,281 | B2 | 11/2013 | Diel et al. |
| 8,677,529 | B2 | 3/2014 | Jackson |
| 8,707,484 | B2 | 4/2014 | Jackson et al. |
| 8,719,979 | B2 | 5/2014 | Jackson |
| 8,826,474 | B2 | 9/2014 | Jackson |
| 8,839,471 | B2 | 9/2014 | Jackson |

(Continued)

FOREIGN PATENT DOCUMENTS

WO WO2017139548 8/2017

*Primary Examiner* — Myles A Throop

(57) ABSTRACT

A frame and patient support are provided, as well as surgical methods using the frame and patient support. The frame and patient support can be used to support and manipulate the patient prior to, during, and after surgery to articulate the patient's body to facilitate stabilization of the patient's spine. The frame and patient support can be configured for rotation about a rotational axis, and the frame and patient support can include a lower-leg-support, an upper-leg-support, a pelvic-support, a torso-support, and a head-and-arm support for supporting corresponding portions of the patient's body.

18 Claims, 31 Drawing Sheets

(56) References Cited

U.S. PATENT DOCUMENTS

| | | | |
|---|---|---|---|
| 8,978,180 B2 | 3/2015 | Jackson | |
| 9,180,062 B2 | 11/2015 | Jackson | |
| 9,186,291 B2 | 11/2015 | Jackson et al. | |
| 9,198,817 B2 | 12/2015 | Jackson | |
| 9,211,223 B2 | 12/2015 | Jackson | |
| 9,226,865 B2 | 1/2016 | Jackson et al. | |
| 9,265,680 B2 | 2/2016 | Sharps et al. | |
| 9,283,084 B1 | 3/2016 | O'Hara | |
| 9,289,342 B2 | 3/2016 | Jackson | |
| 9,295,433 B2 | 3/2016 | Jackson et al. | |
| 9,301,897 B2 | 4/2016 | Jackson | |
| 9,308,145 B2 | 4/2016 | Jackson | |
| 9,339,430 B2 | 5/2016 | Jackson et al. | |
| 9,364,380 B2 | 6/2016 | Jackson | |
| 9,468,576 B2 | 10/2016 | Jackson | |
| 9,504,622 B2 | 11/2016 | Jackson | |
| 9,510,987 B2 | 12/2016 | Jackson et al. | |
| 9,622,928 B2 | 4/2017 | Jackson et al. | |
| 9,636,266 B2 | 5/2017 | Jackson et al. | |
| 9,713,562 B2 | 7/2017 | Perlman et al. | |
| 9,757,300 B2 | 9/2017 | Jackson | |
| 9,849,054 B2 | 12/2017 | Jackson | |
| 9,937,094 B2 | 4/2018 | Jackson et al. | |
| 10,159,618 B2 | 12/2018 | Jackson et al. | |
| 10,470,959 B2 | 11/2019 | Le | |
| 10,500,114 B2 | 12/2019 | Jackson et al. | |
| 10,531,998 B2 | 1/2020 | Jackson et al. | |
| 10,576,006 B2 | 3/2020 | Lim et al. | |
| 10,667,975 B2 | 6/2020 | Jackson et al. | |
| 10,695,252 B2 | 6/2020 | Jackson | |
| 10,874,570 B2 | 12/2020 | Lim et al. | |
| 10,888,481 B2 | 1/2021 | Hoel et al. | |
| 10,888,484 B2 * | 1/2021 | Lim | A61G 13/0036 |
| 10,900,448 B2 | 1/2021 | Lim et al. | |
| 10,945,905 B2 | 3/2021 | Hoel et al. | |
| 10,966,892 B2 | 4/2021 | Lim et al. | |
| 11,020,304 B2 | 6/2021 | Lim et al. | |
| 11,026,857 B2 | 6/2021 | Lim et al. | |
| 11,160,709 B2 * | 11/2021 | Jackson | A61G 13/04 |
| 11,278,462 B2 | 3/2022 | Schwardt et al. | |
| 11,497,670 B2 | 11/2022 | Le | |
| 11,628,114 B2 | 4/2023 | Lim | |
| 11,672,718 B2 | 6/2023 | Lim et al. | |
| 11,850,191 B2 | 12/2023 | Lim et al. | |
| 2004/0133979 A1 | 7/2004 | Newkirk et al. | |
| 2005/0080418 A1 | 4/2005 | Simonson et al. | |
| 2007/0192960 A1 | 8/2007 | Jackson | |
| 2013/0269710 A1 | 10/2013 | Hight et al. | |
| 2014/0109316 A1 * | 4/2014 | Jackson | A61G 13/04 5/607 |
| 2015/0265482 A1 | 9/2015 | Ciblak et al. | |
| 2015/0272681 A1 | 10/2015 | Skripps et al. | |
| 2016/0000627 A1 | 1/2016 | Jackson et al. | |
| 2017/0181908 A1 | 6/2017 | Jackson et al. | |
| 2019/0000705 A1 | 1/2019 | Schwardt et al. | |
| 2021/0330536 A1 | 10/2021 | Lim et al. | |
| 2022/0040021 A1 | 2/2022 | Ebara | |
| 2022/0280242 A1 | 9/2022 | Lim et al. | |
| 2023/0301862 A1 | 9/2023 | Lim et al. | |
| 2024/0074930 A1 | 3/2024 | Lorman et al. | |

* cited by examiner

FRAME AND PATIENT SUPPORT, AND SURGICAL METHODS USING SAME

The present application claims the benefit of U.S. Provisional Application No. 63/544,430, filed Oct. 16, 2023; all of which is incorporated by reference herein.

FIELD OF THE INVENTION

The present disclosure relates to a frame and patient support, and surgical methods using the frame and patient support. The frame and patient support can be used to support and manipulate the patient prior to, during, and after surgery to articulate the patient's body to facilitate stabilization of the patient's spine. The frame and patient support can be configured for rotation about a rotational axis, and the frame and patient support can include a lower-leg-support, an upper-leg-support, a pelvic-support, a torso-support, and a head-and-arm support for supporting corresponding portions of the patient's body. The frame and patient support may be easily interchanged with a variety of table stands or modular table stands to improve useability.

BACKGROUND

Conventional spinal surgery has been used to address and correct some spinal deformities, degeneration, and injuries to improve patient-health outcomes. And specialized surgical tables and surgical componentry have been developed to facilitate such conventional spinal surgery. However, such conventional spinal surgery and the specialized tables developed therefor have some limitations. Such specialized tables oftentimes provide limited access to portions of the patient, and such limited access correspondingly limits access to and stabilization of the patient's spine to a desired degree. Accordingly, there is a need for an improved frame and patient support for supporting a patient before, during, and after surgery. The improved frame and patient support can afford both general and fine adjustment of lower leg portions, upper leg portions, pelvic portions, torso portions, and head and arm portions of the patient to afford improved access to and manipulation of the patient's spine. And such improved access and manipulation of the patient's spine can correspondingly facilitate improve patient-health outcomes resulting from spinal surgery.

SUMMARY

The subject of the present disclosure relates to a frame and patient support, and surgical methods using the frame and patient support for use in treatment of a patient supported by the frame and patient support.

In one aspect, the present disclosure provides a method of utilizing a frame and patient support to support portions of a body of a patient, the method including providing the frame and patient support, the frame and patient support including a frame portion having a first end, an opposite second end, a mid-longitudinal axis extending through the first end and the second end, and a length along the mid-longitudinal axis between the first end and the second end, and a plurality of patient support portions attached relative to the frame portion; supporting portions of a pelvic area of the patient with a pelvic-support portion of the patient support portions moveably attached relative to the frame portion, the pelvic-support portion including at least one bracket support portion, a first arm portion, and a second arm portion, the at least one bracket support portion being moveably attached relative to the frame portion, the first arm portion being moveably attached relative to the at least one bracket support portion, and being moveable between a first position and a second position, and the second arm portion being attached relative to the at least one bracket support portion; adjusting a position of a first pad portion along the first arm portion to support a first portion of the pelvic area of the patient, and adjusting a position of a second pad portion along the second arm portion to support a second portion of the pelvic area of the patient; when the first arm portion is in the first position, supporting the first arm portion with a support portion moveably attached to the at least one bracket support portion; and after at least one of the first pad portion and the second pad portion is positioned to support a corresponding one of the first portion and the second portion of the pelvic area of the patient, moving the first arm portion of the pelvic-support portion from the first position to the second position to move the first pad portion away from the first portion of the pelvic area to provide access to a lateral portion of the patient.

In another aspect, the present disclosure provides a method of utilizing a frame and patient support to support portions of a body of a patient, the method including providing the frame and patient support, the frame and patient support including a frame portion having a first end, an opposite second end, a mid-longitudinal axis extending through the first end and the second end, and a length along the mid-longitudinal axis between the first end and the second end, and a plurality of patient support portions attached relative to the frame portion; supporting portions of a pelvic area of the patient with a pelvic-support portion of the patient support portions attached relative to the frame portion, the pelvic-support portion including at least one bracket support portion, a first arm portion, and a second arm portion, the at least one bracket support portion being attached relative to the frame portion, the first arm portion being moveably attached relative to the at least one bracket support portion, and being moveable between a first position and a second position, and the second arm portion being attached relative to the at least one bracket support portion; adjusting a position of a first pad portion along the first arm portion to support a first portion of the pelvic area of the patient, and adjusting a position of a second pad portion along the second arm portion to support a second portion of the pelvic area of the patient; when the first arm portion is in the first position, supporting the first arm portion with a support portion moveably attached to the at least one bracket support portion; and after at least one of the first pad portion and the second pad portion is positioned to support a corresponding one of the first portion and the second portion of the pelvic area of the patient, moving the support portion away from the first arm portion to remove support from the first arm portion to afford movement of first arm portion, and moving the first arm portion of the pelvic-support portion from the first position to the second position to move the first pad portion away from the first portion of the pelvic area to provide access to a lateral portion of the patient.

In yet another aspect, the present disclosure provides a method of utilizing a frame and patient support to support portions of a body of a patient, the method including providing the frame and patient support, the frame and patient support including a frame portion having a first end, an opposite second end, a mid-longitudinal axis extending through the first end and the second end, and a length along the mid-longitudinal axis between the first end and the second end, and a plurality of patient support portions attached relative to the frame portion; supporting portions of a pelvic area of the patient with a pelvic-support portion of the patient support portions moveably attached relative to the frame portion, the pelvic-support portion including at least one bracket support portion, a first arm portion, and a second arm portion, the at least one bracket support portion being moveably attached relative to the frame portion, the first arm portion being pivotally attached relative to the at least one bracket support portion, and being pivotable between a first position and a second position, and the second arm portion being attached relative to the at least one bracket support portion; adjusting a position of a first pad portion along the first arm portion to support a first portion of the pelvic area of the patient, and adjusting a position of a second pad portion along the second arm portion to support a second portion of the pelvic area of the patient; when the first arm portion is in the first position, supporting the first arm portion with a support portion pivotally attached to the at least one bracket support portion; and after at least one of the first pad portion and the second pad portion is positioned to support a corresponding one of the first portion and the second portion of the pelvic area of the patient, moving the support portion away from the first arm portion to remove support from the first arm portion to afford movement of first arm portion, and moving the first arm portion of the pelvic-support portion from the first position to the second position to move the first pad portion away from the first portion of the pelvic area to provide access to a lateral portion of the patient.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
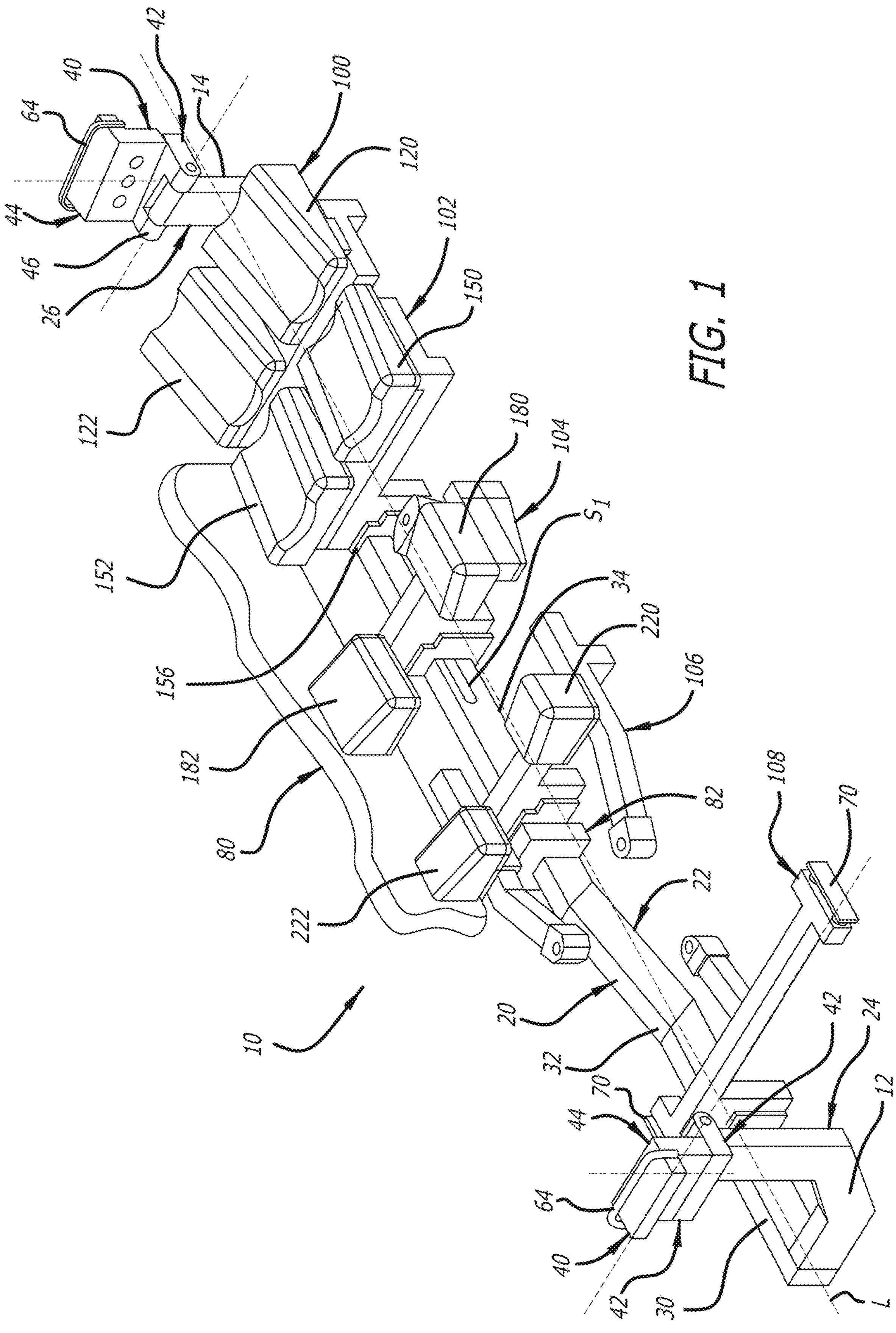
FIG. 1 is a top, first side, first end, perspective view of a first embodiment of a frame and patient support according the present disclosure.
Figure 2:
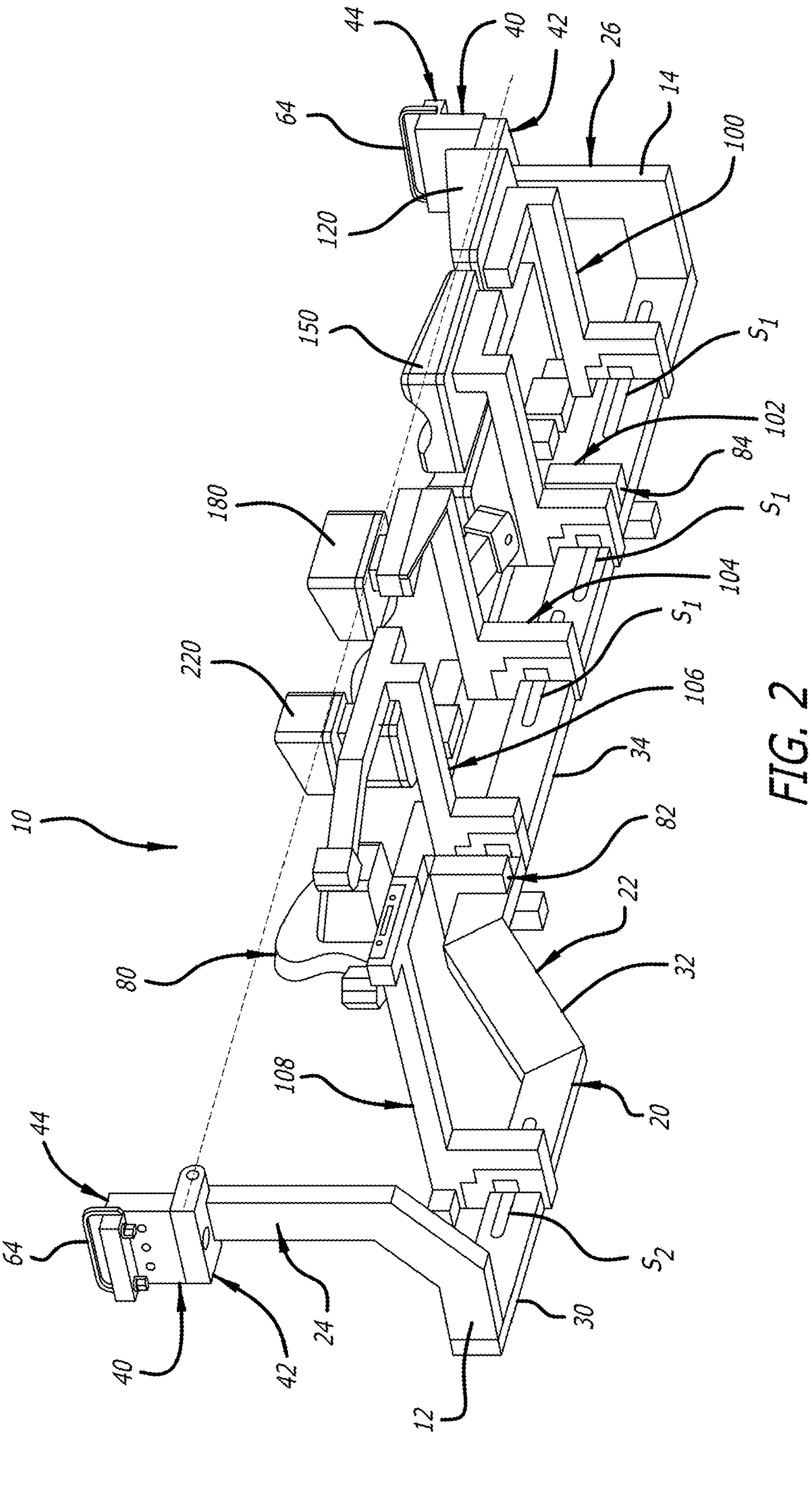
FIG. 2 is a bottom, first side, first end, perspective view of the first embodiment of the frame and patient support of FIG. 1.
Figure 3:
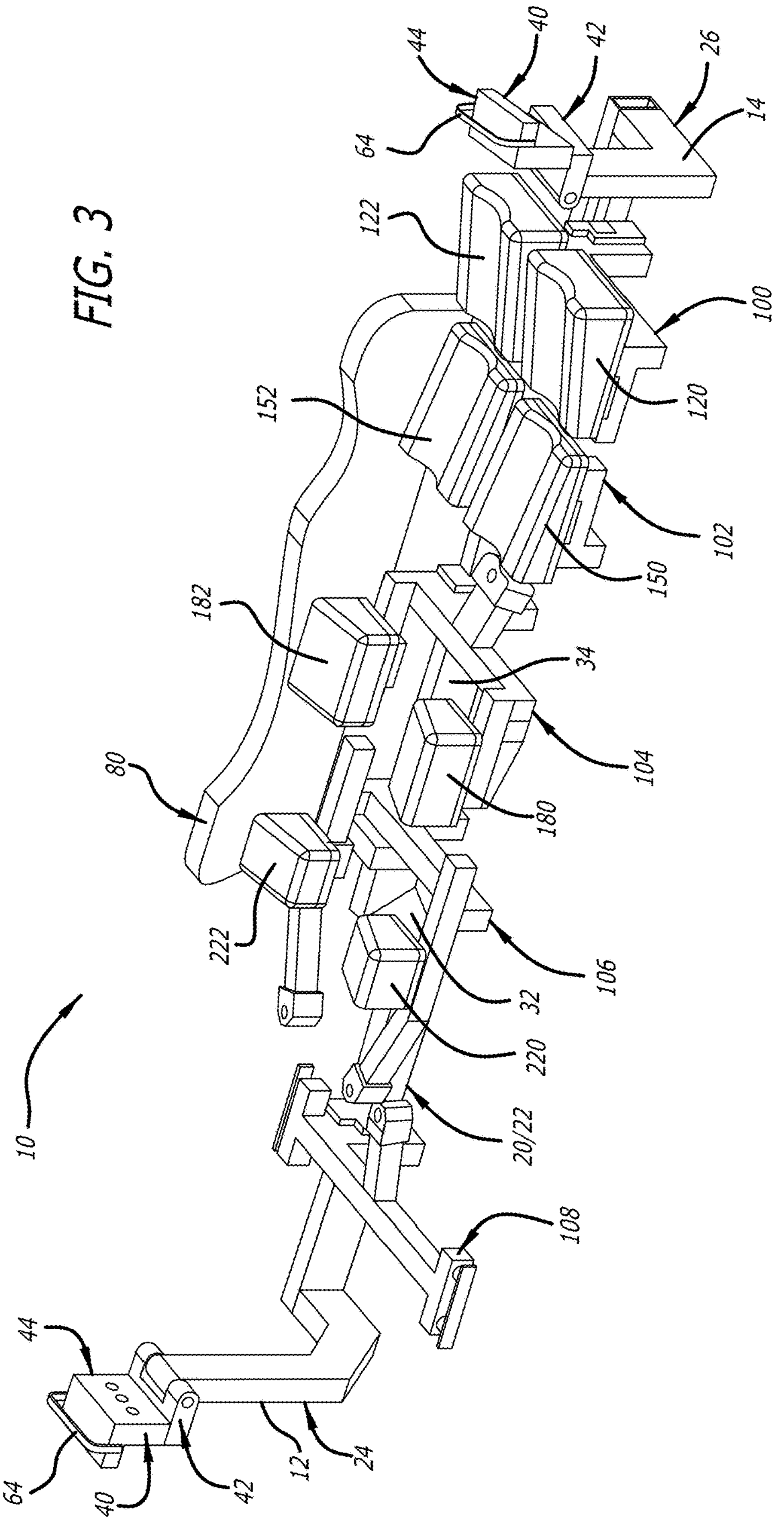
FIG. 3 is a top, first side, second end, perspective view of the first embodiment of the frame and patient support of FIG. 1.

The present disclosure is directed to embodiments of a frame and patient support, and surgical methods using these embodiments for use in treatment of a patient supported by the frame and patient support. While the use of the embodiments of the frame and patient support is described herein with respect to performance of spinal surgery, the use of these embodiments is not limited thereto. The embodiments of the frame and patient support can also, for example, be used in performing hip, upper leg, and/or lower leg surgery.

A first embodiment of the frame and patient support is depicted in FIGS. 1-15, and the first embodiment is generally referenced by the numeral 10. While the frame and patient support 10 (and modified embodiments thereof discussed below) are configured for access to a left lateral side of the patient, mirror-image versions of these embodiments can be provided to alternatively provide access to a right lateral side of the patient.

All or portions of the frame and patient support 10 (and of the modified embodiments thereof discussed below) can be constructed of metallic or non-metallic materials that can be radio-opaque or radio-lucent, or have gradations therebetween. Furthermore, the positions and orientations of the frame and patient support 10 and the various componentry thereof (and the modified embodiments thereof and the various componentry thereof), as well as any support portions therefor, can be automated using robotics. And fluoroscopic, computed tomography (CT), and/or magnetic resonance imaging (MRI) imagers, and/or cameras (e.g., visible light or infrared) can be used for surgical guidance and to provide feedback regarding positions and orientations of the patient and that of the frame and patient support 10 and the various componentry thereof (and the modified embodiments thereof and the various componentry thereof). Such guidance and feedback can be used in controlling the automated portions of the frame and patient support 10 and the various componentry thereof (and the modified embodiments thereof and the various componentry thereof), as well as any support portions. Artificial intelligence (AI) and machine learning can be used as part of the automation and the imaging to beneficially enhance guidance and articulation of the patient and that of the frame and patient support 10 and the various componentry thereof (and the modified embodiments thereof and the various componentry thereof).

The frame and patient support 10 can include a first end 12, an opposite second end 14, and a mid-longitudinal axis L extending through the first end 12 and the second end 14. As discussed below, the frame and patient support 10 can include a plurality of patient support portions for supporting the patient thereon in the prone position. And a frame support 300 (FIGS. 21-22C) can be provided to support the frame and patient support 10, with the first end 12 being supported relative to a first vertical support portion 302 of the frame support and the second end 14 being support relative to a second vertical support portion 304.

As depicted in FIGS. 1, 2, 8, 9, and 14A-14E, for example, the frame and patient support 10 can include a frame 20 having a central beam portion 22, a first end portion 24 attached to one end of the central beam portion 22 adjacent the first end 12, and a second end portion 26 attached to the other end of the central beam portion 22 adjacent the second end 14. When the patient is supported by the frame and patient support 10, the central beam portion 22 can conform to portions of the patient's body. To that end, the central beam portion 22, as depicted in FIGS. 1, 2, 8, 9, and 14A-14E, for example, can include a first portion 30, a second portion 32, and a third portion 34.

As depicted in FIGS. 1, 2, 8, 9, and 14A-14E, for example, the first portion 30 can extend from the first end portion 24 to the second portion 32, the third portion 34 can extend from the second end portion 26 to the second portion 32, and the second portion 32 can transition between the first portion 30 and the third portion 34. The transition afforded by the second portion 32 can afford extension of the first portion 30 underneath the torso of the patient's body when the patient is supported in the prone position on the frame and patient support 10, and afford extension of the third portion 34 along the right lateral side of the patient's body when the patient is supported in the prone position on the frame and patient support 10.

Figure 21:
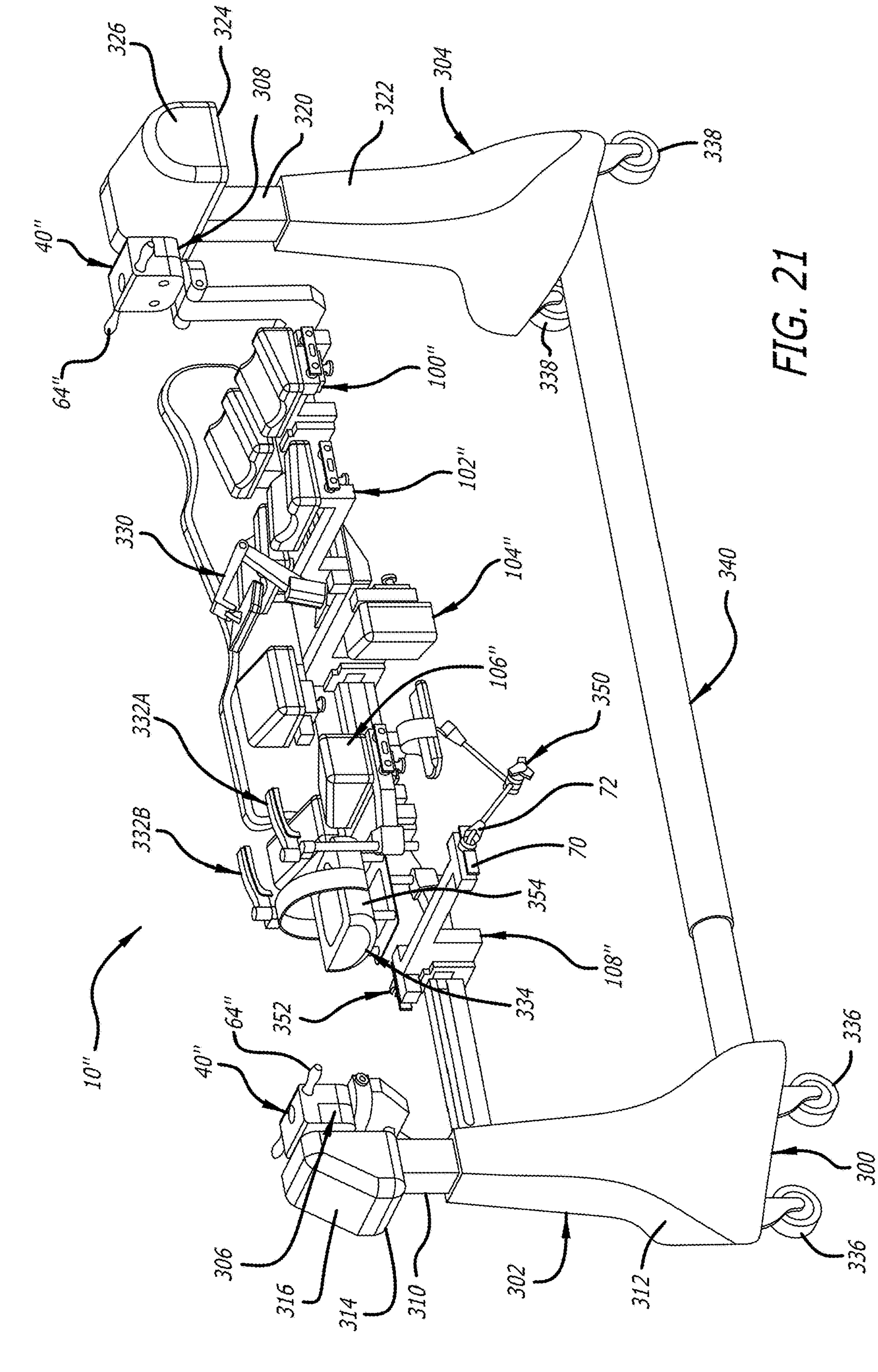
FIG. 21 is a top, first side, first end, perspective view of a third embodiment of a frame and patient support according the present disclosure supported relative to ground by a frame support structure.
Figure 22A:
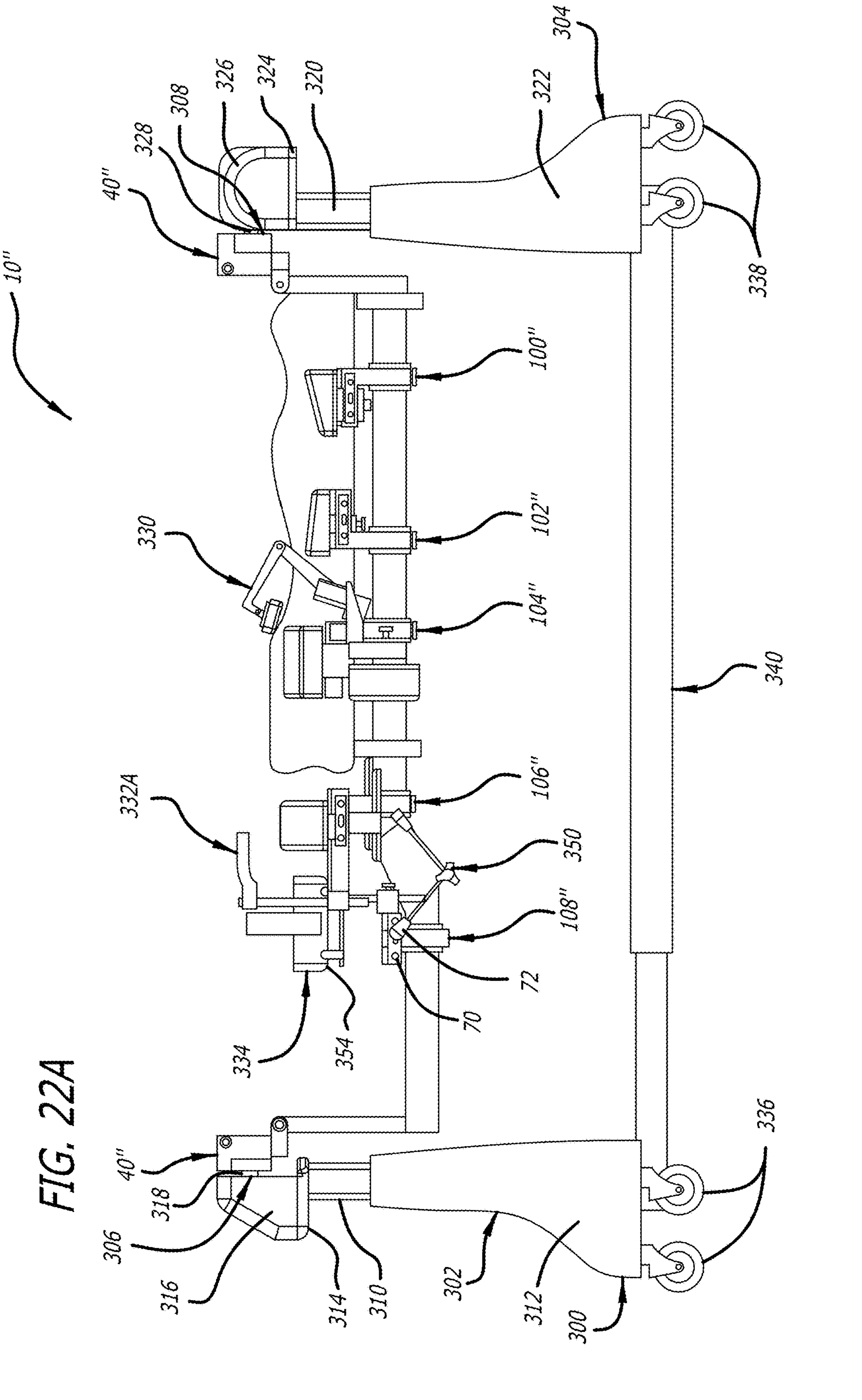
FIG. 22A is a first side, elevational view of the third embodiment of the frame and patient support of FIG. 21 supported by the frame support structure.
Figure 22B:
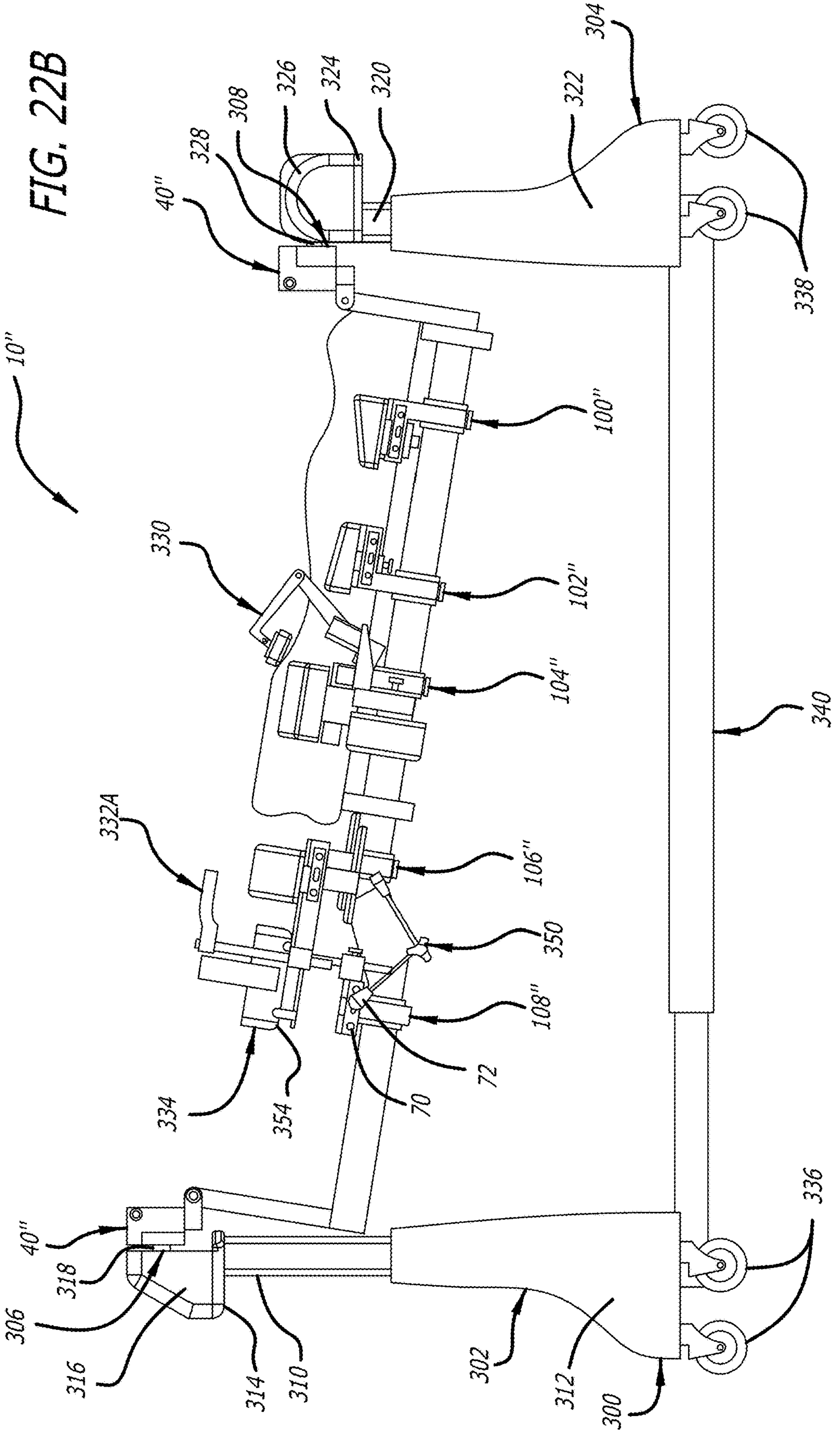
FIG. 22B is a first side, elevational view of the third embodiment of the frame and patient support of FIG. 21 supported by the frame support structure with the frame and patient support in a reverse Trendelenburg position.

Furthermore, the first end portion 24 and the second end portion 26 can include portions extending in planes transverse to the mid-longitudinal axis L, and the configuration of the first end portion 24 and the second end portion 26 can serve to offset the central beam portion 22 from an axis of rotation of the frame 20. The frame 20, as depicted in FIGS. 21 and 22, can be rotatably interconnected relative to the first vertical support portion 302 and the second vertical support portion 304 to afford 360° rotation relative to the first vertical support portion 302 and the second vertical support portion 304 or other support structures therefor. The axis of rotation can extend through portions of the first end portion 24, the second end portion 26, the first vertical support portion 302, and the second vertical support portion 304, and one or more actuators (not shown) can be used to facilitate rotation of the frame and patient support 10 about the axis of rotation. The frame 20 can be moved into various rotational positions via actuation of the one or more actuators, and can be locked in these rotational positions in manual or automated fashion to enhance surgery using the frame and patient support 10. The first end portion 24 and the second end portion 26 also can be configured to cooperate and engage existing modular table stands including, for example, Advanced Table System, Modular Table System, and/or Trios Modular Table System.

To facilitate interconnection of the first end portion 24 to the first vertical support portion 302 and interconnection of the second end portion 26 to the second vertical support portion 304, each of the first end portion 24 and the second end portion 26 can include interconnection attachments 40 (FIGS. 1, 2, 10, and 11, for example) attached thereto. The interconnection attachments 40 can be used to lock ends of the frame 20" to portions attached to the first vertical support portion 302 and the second vertical support portion 304 to facilitate rotation of the frame 20 and a patient supported by the frame and patient support 10. The interconnection attachments 40 are configured to afford first pivotal movements of first end portion 24 and the second end portion 26 about pivotal axes that extend horizontally in FIG. 1, and second pivotal movements of the first end portion 24 and the second end portion 26 about pivotal axes that extend vertically in FIG. 1. The first pivotal movements and the second pivotal movements serve in preventing unwanted binding and/or deflection of the frame 20 during attachment relative to the first vertical support 302 and the second vertical support 304, and during rotation of the frame 20.

Figure 10:
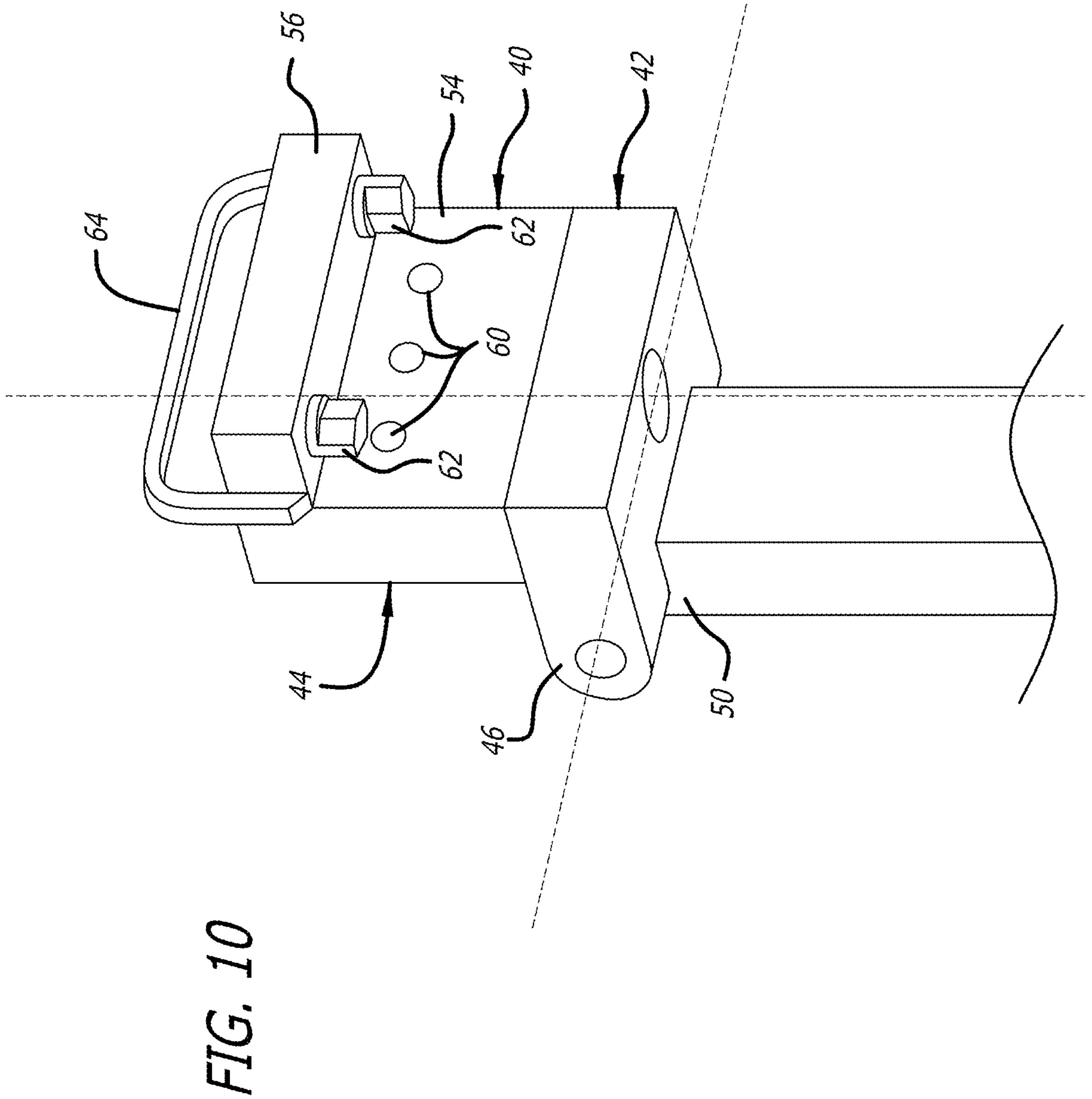
FIG. 10 is an enlarged, bottom, first side, perspective view of an interconnection attachment provided at the first end of the first embodiment of the frame and patient support of FIG. 1.
Figure 11:
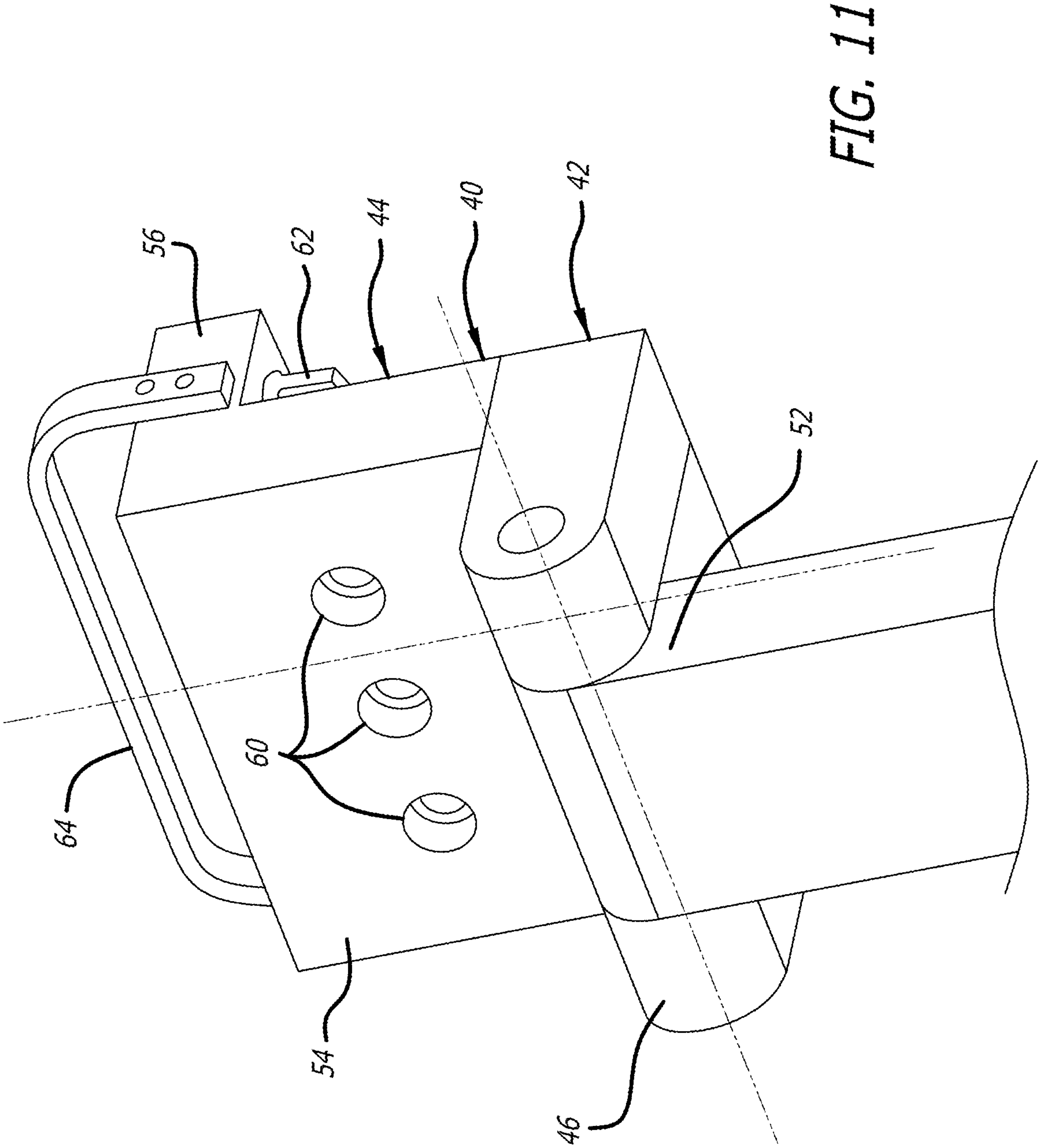
FIG. 11 is an enlarged, bottom, first side perspective view of an interconnection attachment provided at the second end of the first embodiment of the frame and patient support of FIG. 1.
Figure 12:
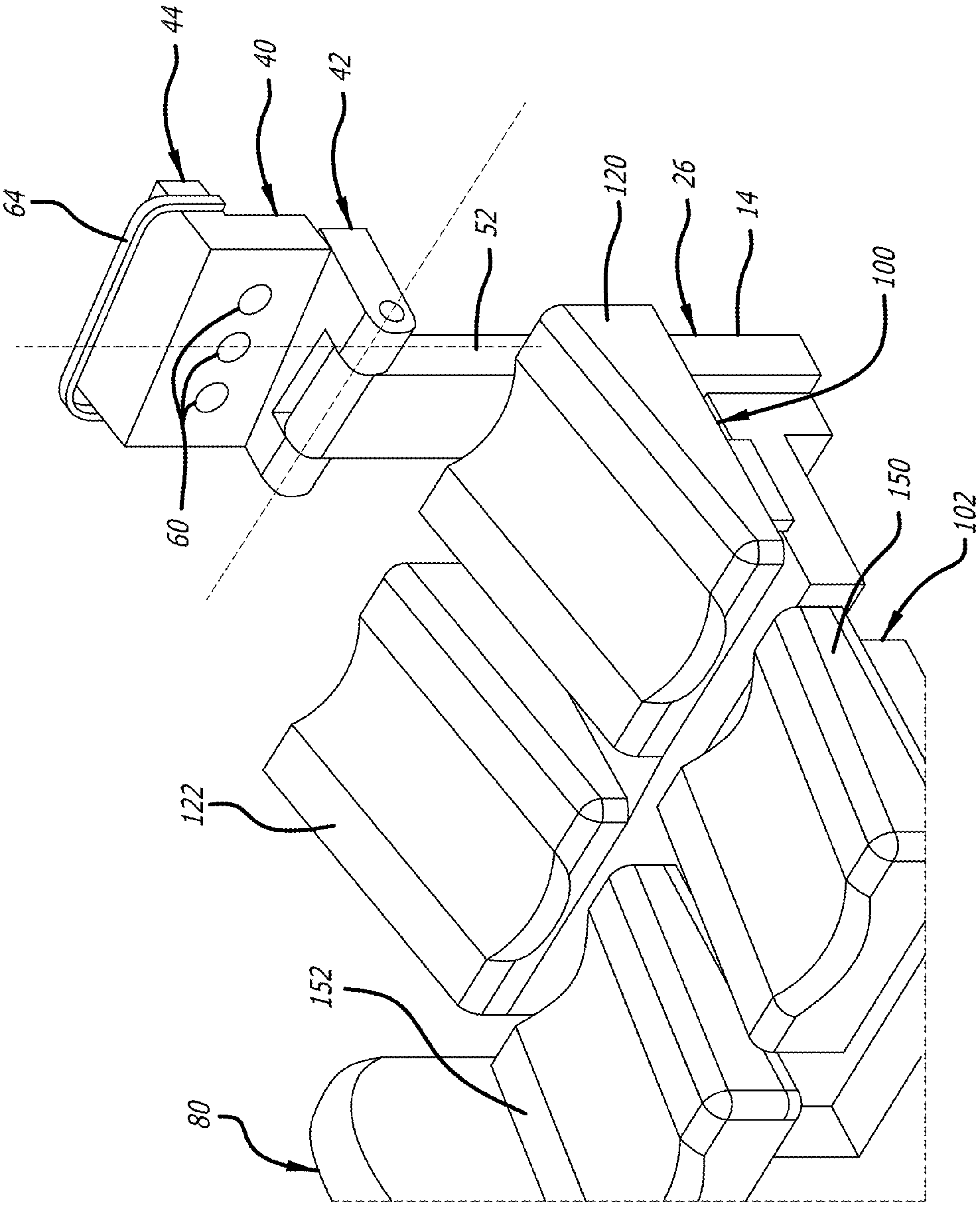
FIG. 12 is an enlarged, top, first side, perspective view of a third portion of the first embodiment of the frame and patient support of FIG. 1.
Figure 13:
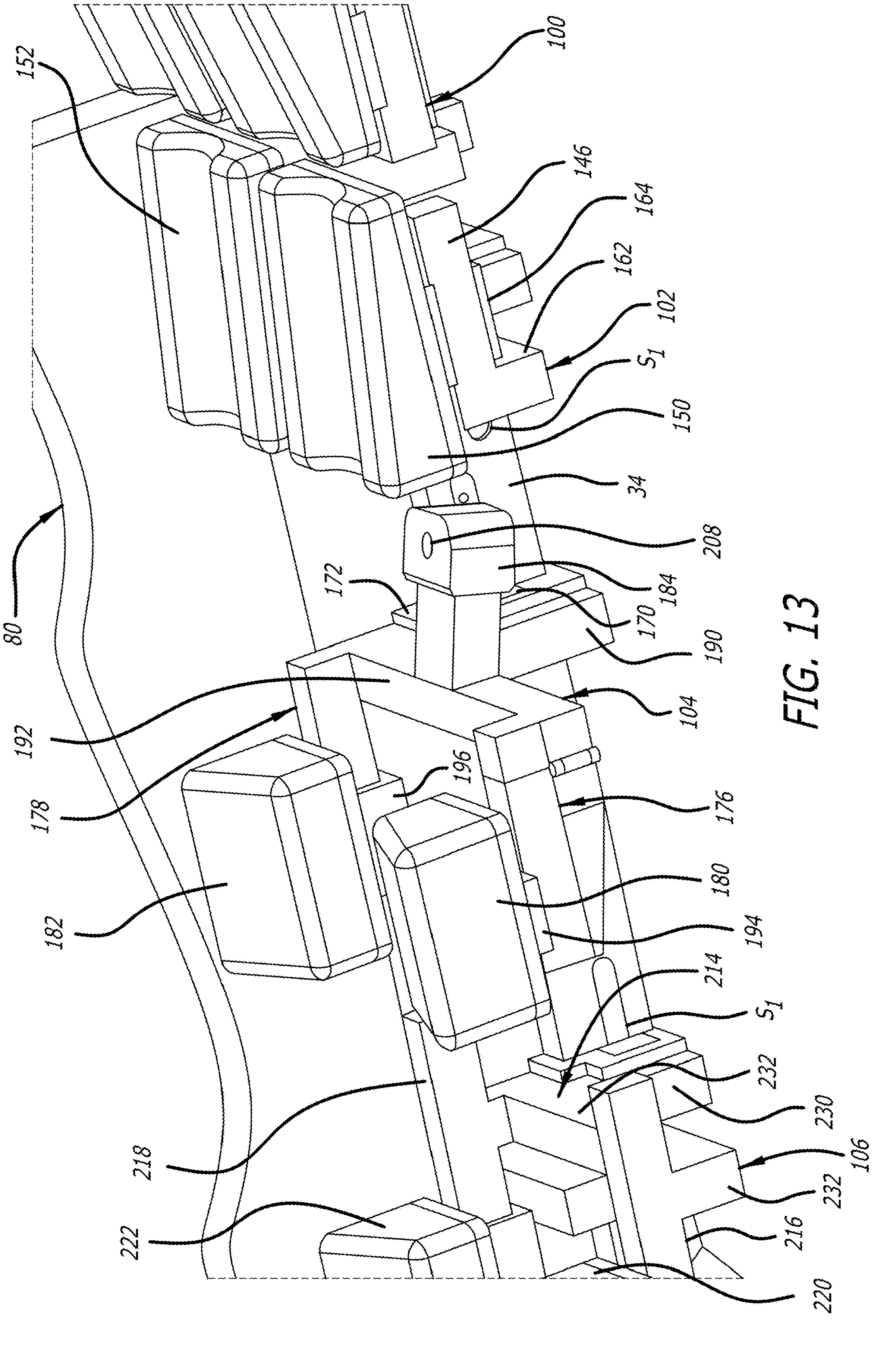
FIG. 13 is an enlarged, top, first side, perspective view of a fourth portion of the first embodiment of the frame and patient support of FIG. 1.

As depicted in FIGS. 10 and 11, for example, each of the interconnection attachments 40 includes a first base portion 42 and a second L-shaped portion 44. To facilitate the first pivotal movements, each of the base portions 42 can include a first end 46 that forms a clevis/tang attachment with an end 50 of the first end portion 24 or with an end 52 of the second end portion 26. To illustrate, one of the end 50 of the first end portion 24, and the first end 46 of the base portion 42 of the interconnection attachment 40 attached to the first end portion 24 can be a clevis and the other can be a tang to facilitate the first pivotal movement of the first end portion 24. And, one of the end 52 of the second end portion 26, and the first end 46 of the base portion 42 of the interconnection attachment 40 attached to the second end portion 26 can be a clevis and the other can be a tang to facilitate the first pivotal movement of the second end portion 26. Furthermore, to facilitate the second pivotal movements, the L-shaped portions 44 can be pivotally attached to the base portion 42 of each of the interconnection attachments 40. And, as depicted in FIGS. 1, 10, and 11, for example, each of the L-shaped portions 44 include an upstanding portion 54 and an overhang portion 56 with the upstanding portions 54 being pivotally attached to the base portions 42 of the interconnection attachments 40.

To facilitate attachment with the first vertical support portion 302 and the second vertical support portion 304, the upstanding portions 54 of each of the interconnection attachments 40, as depicted in FIGS. 10 and 11, for example, include various apertures 60 for receiving fasteners, and the overhang portions 56 of each of the interconnection attachments 40 can include downwardly-depending protrusions 62. The protrusions 62 can each include similar or different sizes and/or shapes to facilitate receipt thereof in complimentary features formed in portions attached to the first vertical support portion 302 and the second vertical support portion 304. The protrusions 62 and the receipt thereof in such complimentary features can be used to dock and lock the interconnection attachments 40 to such portions attached to the first vertical support portion 302 and the second vertical support portion 304. As depicted in FIG. 10, the protrusions 62 have similar exterior sizes and shapes, but the protrusions are not so limited. The protrusions 62 can have different exterior sizes and shapes that can be oriented at different angles (including at) 90° with respect to one another. The different exterior sizes and shapes of the protrusions 62 can be matched to the complimentary features of the first vertical support portion 302 and the second vertical support portion 304, and the different orientations of the protrusions 62 can make it easier to dock and lock with the complimentary features of the first vertical support portion 302 and the second vertical support portion 304.

As depicted in FIGS. 10 and 11, for example, the interconnection attachments 40 also can include handles 64 so that the first end portion 24 and the second end portion 26 can be manipulated into position to the first vertical support portion 302 and the second vertical support portion 304, respectively. In doing so, the protrusions 62 of the interconnection attachments 50 can be received in the complimentary features provided in the first vertical support portion 302 and the second vertical support portion 304, and fasteners (not shown) can be inserted through the various apertures 60 and into additional complimentary features formed in the first vertical support portion 302 and the second vertical support 304 portion to secure attachment of the first end portion 24 to the first vertical support portion 302 and attachment of the second end portion 26 to the second vertical support portion 304. The secure attachment of the first end portion 24 and the second end portion 26 to the first vertical support portion 302 and the second vertical support portion 304, respectively, using the interconnection attachments 40 allow for rotation of the frame portion 20 about the axis of rotation thereof.

As depicted in FIGS. 1 and 14A-14E, each of the first portion 30 and the third portion 34 of the central beam portion 22 are configured to support the plurality of patient support portions at various adjustable locations therealong. In addition to the plurality of patient support portions, the first portion 30, the third portion 34, and the plurality of patient support portions can be used to support various rails 70 (FIGS. 1-3, 8, 21, 22A-22C, and 24) and Clark sockets 72 (FIGS. 21 22C) attached to the rails 70 that can be used to support some additional equipment and accessories.

Figure 8:
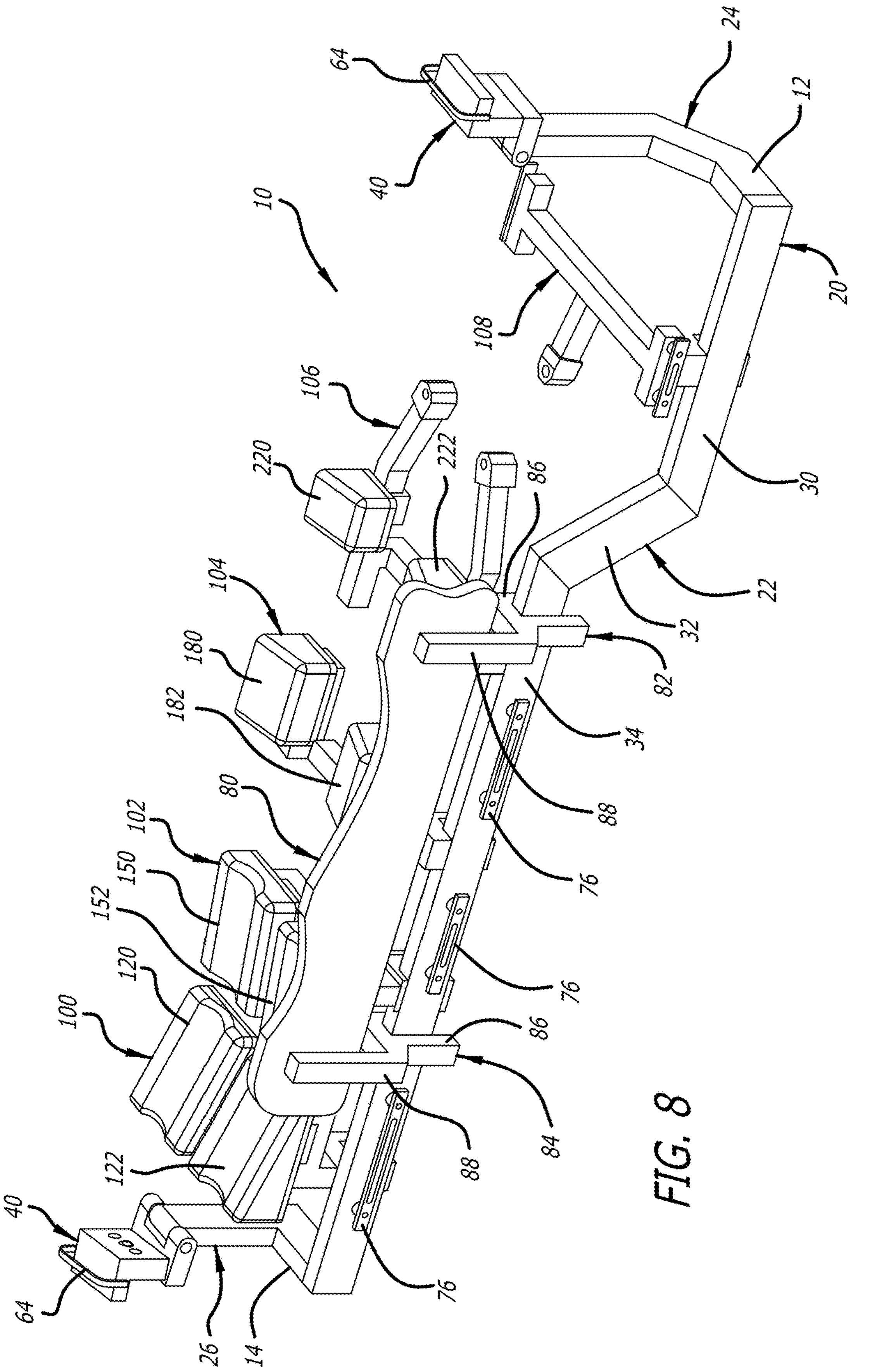
FIG. 8 is a top, second side, first end, perspective view of the first embodiment of the frame and patient support of FIG. 1.
Figure 9:
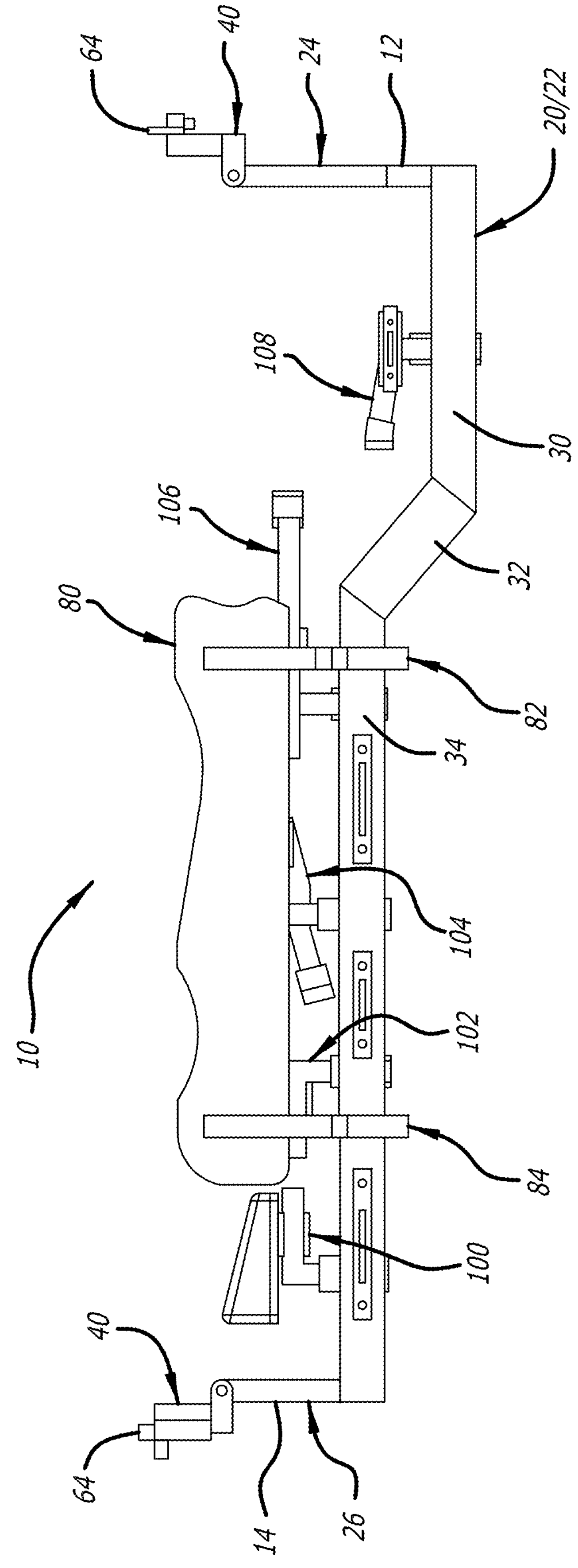
FIG. 9 is a second side, elevational view of the first embodiment of the frame and patient support of FIG. 1.

As depicted in FIGS. 8 and 9, for example, the first portion 30 and/or the third portion 34 also can be used to support a side-board 80. To illustrate, the side-board 80 can be supported by a first bracket 82 and a second bracket 84 that each include a base portion 86 that can be U-shaped and an extension portion 88 extending upwardly from the base portion 86. The base portions 86 of the first bracket 82 and the second bracket 84 can be received over the first portion 30 and/or the third portion 34, and the side-board 80 can be attached to the extension portions 88 of the first bracket 82 and the second bracket 84. The base portions 86 can be moved along the first portion 30 or the third portion 34 to position the side-board 80 relative to the plurality of patient support portions and the patient positioned thereon. As depicted in FIGS. 8 and 9, for example, the base portion 86 are positioned along the third portion 34 to facilitate support (if necessary) of a lower portion of the patient's body using the side-board 80. The base portions 86 can be locked into position on the first portion 30 and/or the third portion 34 to maintain the position of the side-board 80.

The plurality of patient support portions, as depicted in FIGS. 1-3 and 14A-14E, for example, can include a lower-leg-support 100, an upper-leg-support 102, a pelvic-support 104, a torso-support 106, and a head-and-arm-support 108. The lower-leg-support 100, the upper-leg-support 102, the pelvic-support 104, the torso-support 106, and the head-and-arm-support 108 can each be moveably attached relative to the frame 20 via slidable receipt of portions thereof in one or more slots formed in the frame 20. Alternatively, desired ones of the lower-leg-support 100, the upper-leg-support 102, the pelvic-support 104, the torso-support 106, and the head-arm-support 108 can be fixedly attached relative to the frame 20, while the others of the lower-leg-support 100, the upper-leg-support 102, the pelvic-support 104, the torso-support 106, and the head-arm-support 108 can be moveably attached to the frame 20 via the slidable receipt of the portions thereof in the one or more slots formed in the frame 20.

The lower-leg-support 100, the upper-leg-support 102, the pelvic-support 104, and the torso-support 106 can each be supported relative to the third portion 34 of the frame portion 20, and the head-and-arm-support 108 can be supported relative to the first portion 30 of the frame portion 20. To that end, the third portion 34 can include various slots S1 for facilitating slidable engagement of the lower-leg-support 100, the upper-leg-support 102, the pelvic-support 104, and the torso-support 106 to the third portion 34. Such slidable engagement affords positioning and repositioning of the lower-leg-support 100, the upper-leg-support 102, the pelvic-support 104, and the torso-support 106 along the third portion 34 to accommodate patients of different heights.

Figure 14A:
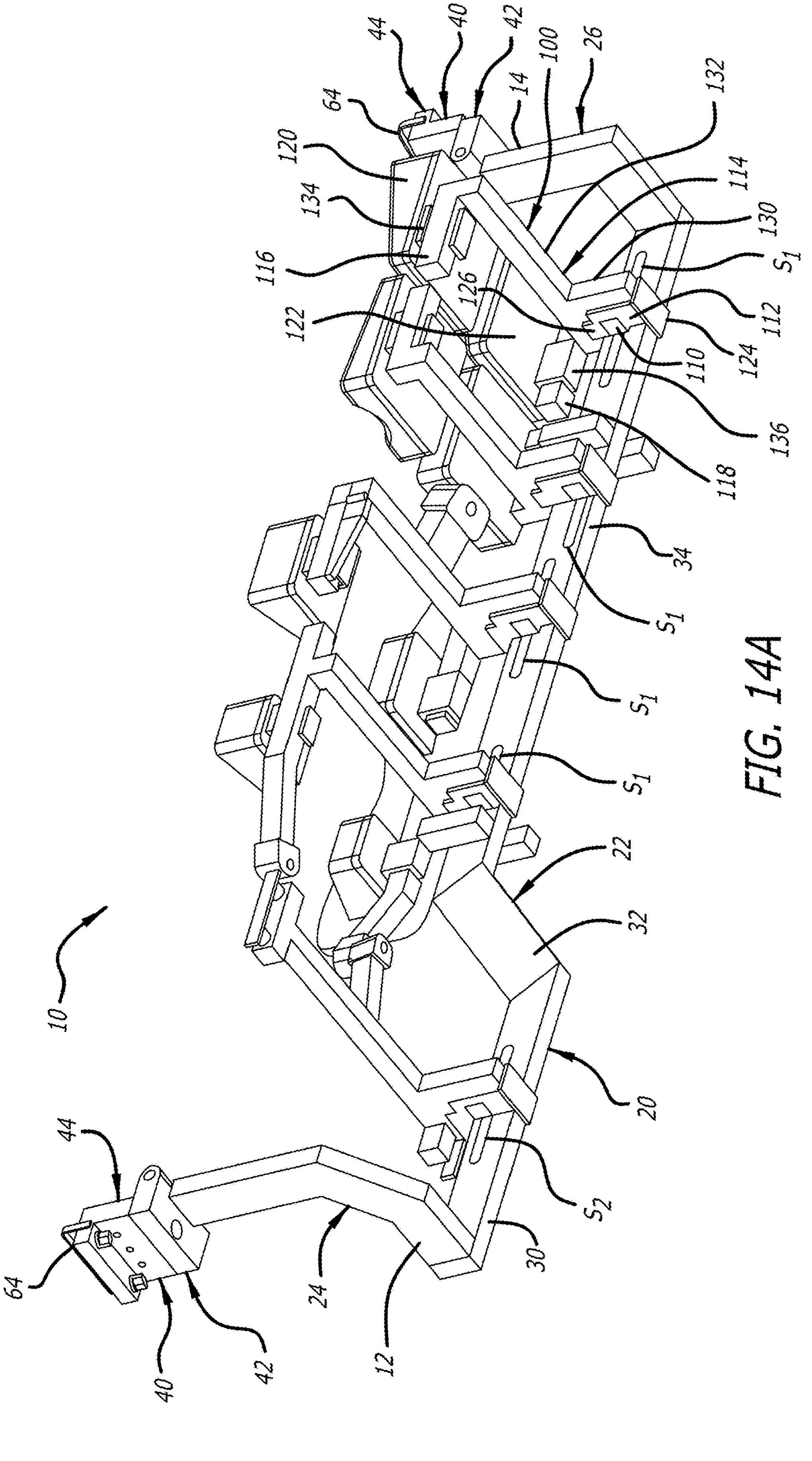
FIG. 14A is a bottom, first side, first end, perspective view of the first embodiment of the frame and patient support of FIG. 1.

The lower-leg-support 100 can be used to support at least portions of the patient's lower legs, and, as depicted in FIG. 14A, for example, includes a first bracket portion 110, a second bracket portion 112, a base portion 114, a first arm portion 116, a second arm portion 118, a first pad portion 120, and a second pad portion 122. A first portion of the first bracket portion 110 can be received in a complimentary-shaped structure within a first portion of the interior of the third portion 34 and extends through one of the slots S1, and using, for example, a slide bearing having bushing and carriage, is slidably moveable with respect to the third portion 34. The interaction of the first bracket portion 110 within the interior of the third portion 34 serves to counteract moments of inertia caused by the supporting of the portions of the patient's lower legs by the lower-leg-support 100. A second portion of the first bracket portion 110 is attached to the first portion thereof and is moveable on the exterior of the third portion 34, and the second bracket portion 112 can be attached to the second portion of the first bracket portion 110. The second bracket portion 112 can be used to secure attachment of the first bracket portion 110 to the third portion 34 in a selected location via receipt of one or more fasteners (not shown) through a first engagement tongue 124 thereof to contact a lower portion of the third portion 34, and/or a second engagement tongue 126 there to contact an upper portion of the third portion 34.

The second bracket portion 112 is attached to the first bracket portion 110, and, as depicted in FIG. 14A, supports the base portion 114 relative to the first bracket portion 110. The base portion 114 can be fixedly or pivotally attached relative to the second bracket portion 112. The base portion 114 can include a first portion 130 that can be oriented vertically, and a second portion 132 that can be oriented horizontally. The first portion 130 of the base portion 114 can be fixedly or pivotally attached relative to the second bracket portion 112, and the second portion 132 of the base portion 114 can effectively extend outwardly from the third portion 34. The second portion 132 of the base portion 114 can support each of the first arm portion 116 and the second arm portion 118 at opposite ends thereof, and the first arm portion 116 and the second arm portion 118 can extend from the second portion 132 toward the first end 12. While the first arm portion 116 and the second arm portion 118 are shown as being aligned with the mid-longitudinal axis L, the first arm portion 116 and the second arm portion 118 can alternatively be angled inwardly or outwardly and/or upwardly or downwardly relative to the mid-longitudinal axis L. These angles of the first arm portion 116 and the second arm portion 118 can be fixed or variable (via adjustable attachment thereof to the second portion 132) can be used to accommodate different types of surgeries, as well as differently sized patients and/or patients having ailments, injuries, and/or deformities.

The first pad portion 120 can support a portion of the patient's lower left leg, can be rotatably and/or slidably attached to a first slidable member 134, and can be moveably supported relative to the first arm portion 116 using the first slidable member 134 slidably moveable along the first arm portion 116; and the second pad portion 122 can support a portion of the patient's lower right leg, can be rotatably and/or slidably attached to a second slidable member 136, and can be moveably supported relative to the second arm portion 118 using the second slidable member 136 slidably moveable along the second arm portion 118. The first pad portion 120 and the second pad portion 122 can be rotated independently of one another, slidable independently of one another inwardly and outwardly relative to one another, and slidably moved independently of one another in directions aligned or substantially aligned with the mid-longitudinal axis (via the first slidable member 134 and the second slidable member 136), and can be secured in selected locations along the first arm portion 116 and the second arm portion 118, respectively, using fasteners (not shown) received therethrough and engaging the first arm portion 116 and the second arm portion 118. To accommodate patients having different heights, general adjustment can be provided by positioning and repositioning the location of the lower-leg-support 100 relative to the third portion 34, and then finer adjustment can be provided by independent positioning and repositioning the locations of the first pad portion 120 and the second pad portion 122 to additionally accommodate the specific anatomy of the patient. And to accommodate patients having different ailments, injuries, and/or deformities, the orientations (slidable or rotational) of the first pad portion 120 and the second pad portion 122 can be adjusted to accommodate these ailments, injuries, and/or deformities. As such, the adjustability of the first pad portion 120 and the second pad portion 122 can be symmetrical or asymmetrical relative to one another about the mid-longitudinal axis L, and the asymmetry can be used to accommodate patients with different ailments, injuries, and/or deformities.

Figure 14B:
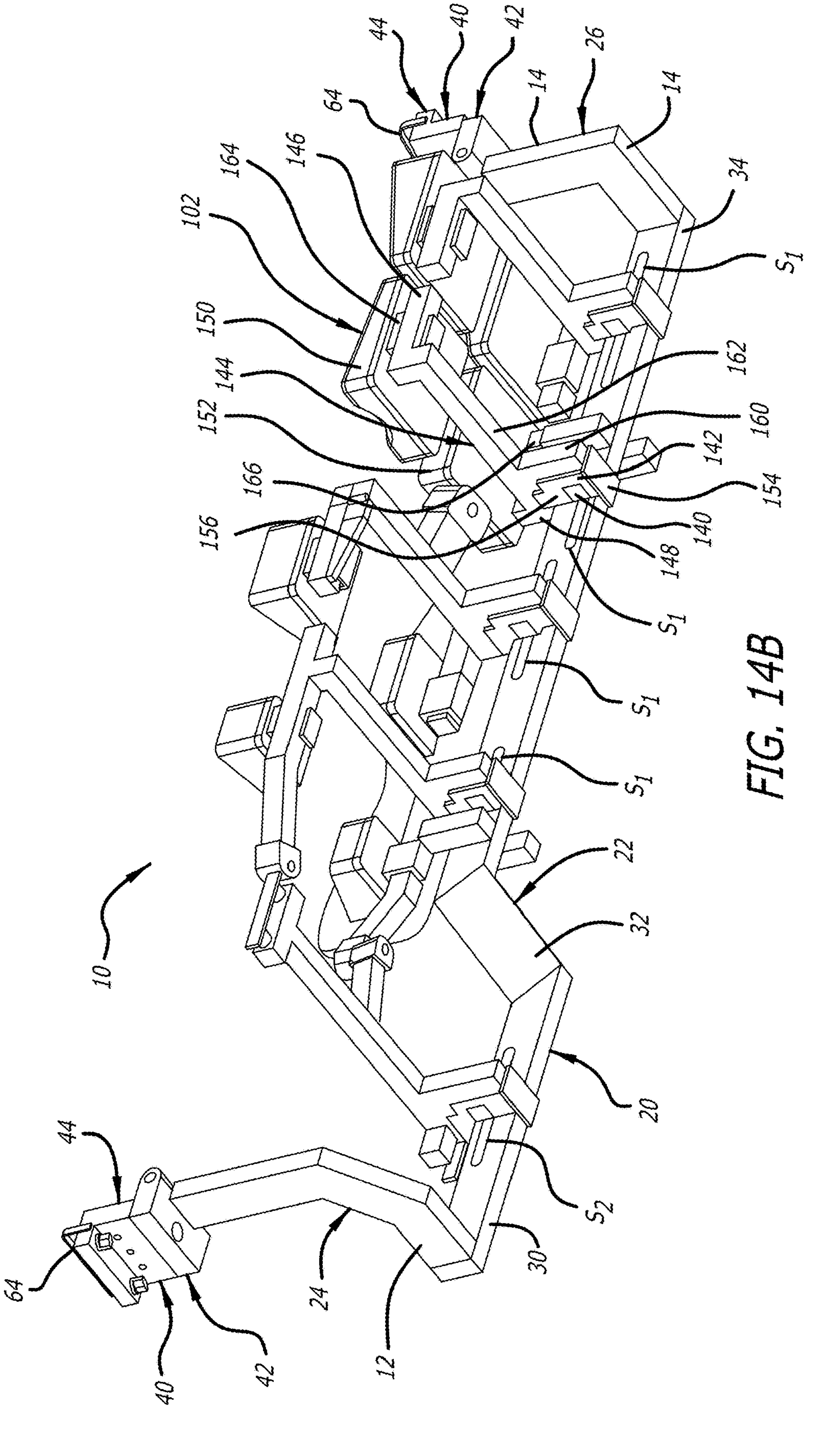
FIG. 14B is a bottom, first side, first end, perspective view of the first embodiment of the frame and patient support of FIG. 1 similar to FIG. 14A.

The upper-leg-support 102 can be used to support at least portions of the patient's upper legs, and, as depicted in FIG. 14B, for example, includes a first bracket portion 140, a second bracket portion 142, a base portion 144, a first arm portion 146, a second arm portion 148, a first pad portion 150, and a second pad portion 152. A first portion of the first bracket portion 140 can be received in a complementarily-shaped structure within a second portion of the interior of the third portion 34 and extends through one of the slots S1, and using, for example, a slide bearing having bushing and carriage, is slidably moveable with respect to the third portion 34. The interaction of the first bracket portion 140 within the interior of the third portion 34 serves to counteract moments of inertia caused by the supporting of the portions of the patient's upper legs by the upper-leg-support 102 A second portion of the first bracket portion 140 is attached to the first portion thereof and is moveable on the exterior of the third portion 34, and the second bracket portion 142 can be attached to the second portion of the first bracket portion 140. The second bracket portion 142 can be used to secure attachment of the first bracket portion 140 (and remaining portions of the upper-leg-support 102) to the third portion 34 in a selected location via receipt of one or more fasteners (not shown) through a first engagement tongue 154 thereof to contact a lower portion of the third portion 34, and/or a second engagement tongue 156 thereof to contact an upper portion of the third portion 34.

The second bracket portion 142 is attached to the first bracket portion 140, and, as depicted in FIG. 14B, supports the base portion 144 relative to the first bracket portion 140. The base portion 144 can be fixedly or pivotally attached relative to the second bracket portion 142. The base portion 144 can include a first portion 160 that can be oriented vertically, and a second portion 162 that can be oriented horizontally. The first portion 160 of the base portion 144 can be fixedly or pivotally attached relative to the second bracket portion 142, and the second portion 162 of the base portion 144 can effectively extend outwardly from the third portion 34. The second portion 162 of the base portion 144 can support each of the first arm portion 146 and the second arm portion 148 at opposite ends thereof, and portions of the first arm portion 146 and the second arm portion 148 can extend from the second portion 162 toward the second end 14. While the first arm portion 146 and the second arm portion 148 are shown as being aligned with the mid-longitudinal axis L, the first arm portion 146 and the second arm portion 148 can alternatively be angled inwardly or outwardly and/or upwardly or downwardly relative to the mid-longitudinal axis L. These angles of the first arm portion 146 and the second arm portion 148 can be fixed or variable (via adjustable attachment thereof to the second portion 162) can be used to position the first pad portion 150 and the second pad portion 152 to accommodate different types of surgeries, as well as differently sized patients and/or patients having ailments, injuries, and/or deformities.

The first pad portion 150 can support a portion of the patient's upper left leg, can be rotatably and/or slidably attached to a first slidable member 164, and can be moveably supported relative to the first arm portion 146 using the first slidable member 164 slidably moveable along the first arm portion 146; and the second pad portion 152 can support a portion of the patient's upper right leg, can be rotatably and/or slidably attached to a second slidable member 166, and can be moveably supported relative to the second arm portion 148 using the second slidable member 166 slidably moveable along the second arm portion 148. The first pad portion 150 and the second pad portion 152 can be rotated independently of one another, slidable independently of one another inwardly and outwardly relative to one another, and slidably moved independently of one another in directions aligned or substantially aligned with the mid-longitudinal axis (via the first slidable member 164 and the second slidable member 166), and can be secured in selected locations along the first arm portion 146 and the second arm portion 148, respectively, using fasteners (not shown) received therethrough and engaging the first arm portion 146 and the second arm portion 148. To accommodate patients having different heights, general adjustment can be provided by positioning and repositioning the location of the upper-leg-support 102 relative to the third portion 34, and then finer adjustment can be provided by independent positioning and repositioning the locations of the first pad portion 150 and the second pad portion 152 to additionally accommodate the specific anatomy of the patient. And to accommodate patients having different ailments, injuries, and/or deformities, the orientations (slidable or rotational) of the first pad portion 150 and the second pad portion 152 can be adjusted to accommodate these ailments, injuries, and/or deformities. As such, the adjustability of the first pad portion 150 and the second pad portion 152 can be symmetrical or asymmetrical relative to one another about the mid-longitudinal axis L, and the asymmetry can be used to accommodate patients with different ailments, injuries, and/or deformities.

Figure 14C:
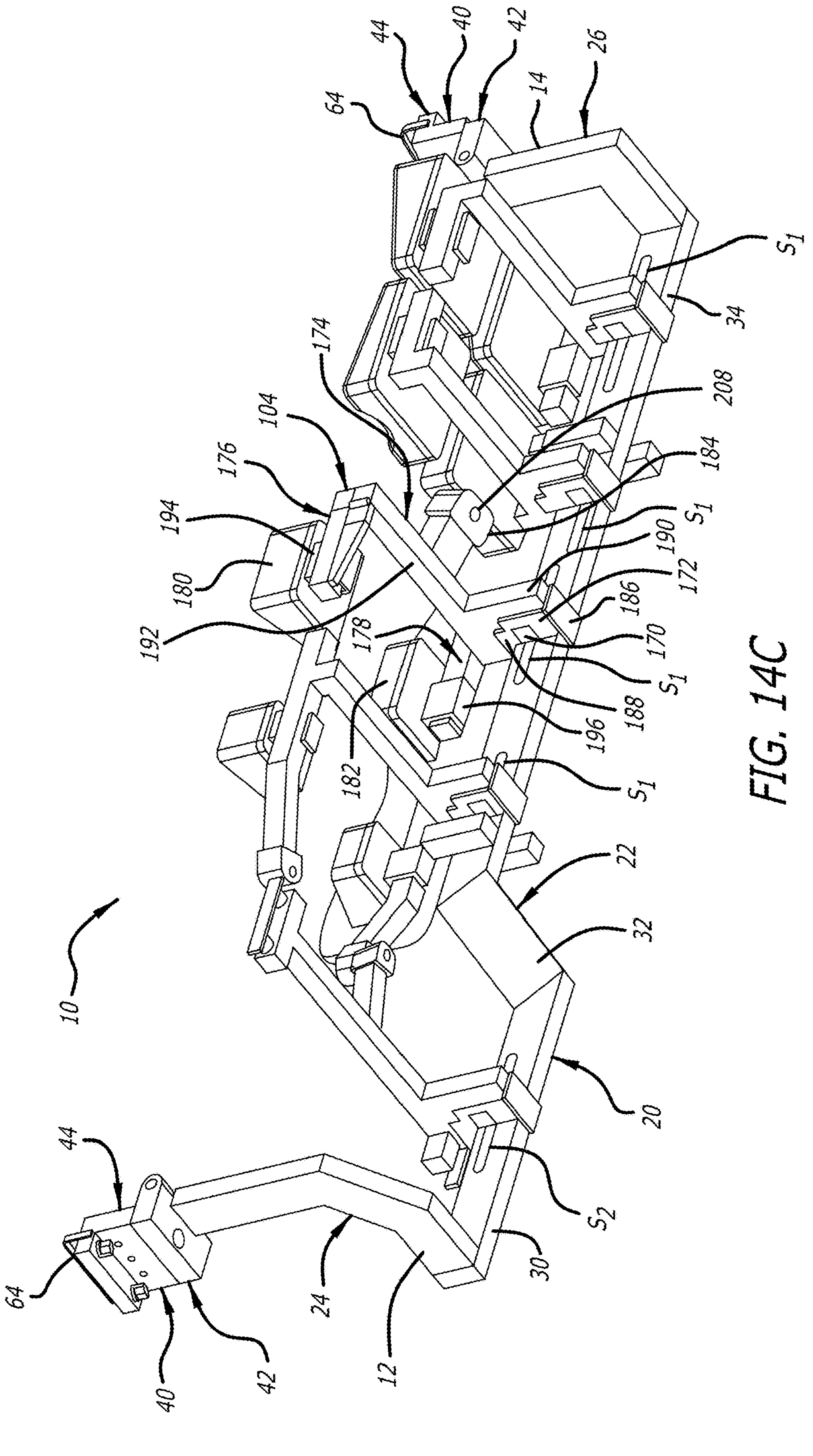
FIG. 14C is a bottom, first side, first end, perspective view of the first embodiment of the frame and patient support of FIG. 1 similar to FIGS. 14A and 14B.

The pelvic-support 104 can be used to support at least portions of the patient's pelvis or pelvic area, and, as depicted in FIG. 14C, for example, includes a first bracket portion 170, a second bracket portion 172, a base portion 174, a first arm portion 176, a second arm portion 178, a first pad portion 180, a second pad portion 182, and an extension portion 184. The extension portion 184 can include an end portion that can be structurally reinforced and mechanically durable, and this end portion can be removable and/or replaceable, so that any connection apertures formed therein (or other connection mechanism) can remain mechanically sound via remachining or replacement. A first portion of the first bracket portion 170 can be received in a complementarily-shaped structure within a third portion of the interior of the third portion 34 and extends through one of the slots S1, and using, for example, a slide bearing having bushing and carriage, is slidably moveable with respect to the third portion 34. The interaction of the first bracket portion 170 within the interior of the third portion 34 serves to counteract moments of inertia caused by the supporting of the portions of the patient's pelvis or pelvic area by the pelvic-support 104. A second portion of the first bracket portion 170 is attached to the first portion thereof and is moveable on the exterior of the third portion 34, and the second bracket portion 172 can be attached to the second portion of the first bracket portion 170. The second bracket portion 172 can be used to secure attachment of the first bracket portion 170 (and remaining portions of the pelvic-support 104) to the third portion 34 in a selected location via receipt of one or more fasteners (not shown) through a first engagement tongue 186 thereof to contact a lower portion of the third portion 34, and/or a second engagement tongue 188 thereof to contact an upper portion of the third portion 34.

The second bracket portion 172 is attached to the first bracket portion 170, and, as depicted in FIG. 14C, supports the base portion 174 relative to the first bracket portion 170. The base portion 174 can be fixedly or pivotally attached relative to the second bracket portion 172. The base portion 174 can include a first portion 190 that can be oriented vertically, and a second portion 192 that can be oriented horizontally. The first portion 190 of the base portion 174 can be fixedly or pivotally attached relative to the second bracket portion 172, and the second portion 192 of the base portion 174 can effectively extend outwardly from the third portion 34. The second portion 192 of the base portion 174 can support each of the first arm portion 176 and the second arm portion 178 at opposite ends thereof, and portions of the first arm portion 176 and the second arm portion 178 can extend from the second portion 192 toward the first end 12. While the first arm portion 176 and the second arm portion 178 are shown as being aligned with the mid-longitudinal axis L, the first arm portion 176 and the second arm portion 178 can alternatively be angled inwardly or outwardly and/or upwardly or downwardly relative to the mid-longitudinal axis L. These angles of the first arm portion 176 and the second arm portion 178 can be fixed or variable (via adjustable attachment thereof to the second portion 192) can be used to position the first pad portion 180 and the second pad portion 182 to accommodate different types of surgeries, as well as differently sized patients and/or patients having ailments, injuries, and/or deformities.

The first pad portion 180 can support a left portion of the patient's pelvis or pelvic area, and can be moveably supported relative to the first arm portion 176 using a first slidable member 194 slidably moveable along the first arm portion 176; and the second pad portion 182 can support a right portion of the patient's pelvis or pelvic area, and can be moveably supported relative to the second arm portion 178 using a second slidable member 196 slidably moveable along the second arm portion 178. The first pad portion 180 and the second pad portion 182 can each include an integrated plate portion that is rotatably and/or slidably attached to a corresponding one of the first slidable member 194 and the second slidable member 196. The first pad portion 180 and the second pad portion 182 can be rotated independently of one another, slidable independently of one another inwardly and outwardly relative to one another, and slidably moved independent of one another in directions aligned or substantially aligned with the mid-longitudinal axis (via the first slidable member 194 and the second slidable member 196), and can be secured in selected locations along the first arm portion 176 and the second arm portion 178, respectively, using fasteners (not shown) received therethrough and engaging the first arm portion 176 and the second arm portion 178. Furthermore, the rotational and/or slidable positions of the first pad portion 180 and the second pad portion 182 can be secured in selected rotational or slidable positions. As such, to accommodate patients having different heights, general adjustment can be provided by positioning and repositioning the location of the pelvic-support 104 relative to the third portion 34, and then finer adjustment can be provided by independent positioning and repositioning the locations of the first pad portion 180 and the second pad portion 182 to additionally accommodate the specific anatomy of the patient. And to accommodate patients having different ailments, injuries, and/or deformities, the orientations (slidable or rotational) of the first pad portion 180 and the second pad portion 182 can be adjusted to accommodate these ailments, injuries, and/or deformities. As such, the adjustability of the first pad portion 180 and the second pad portion 182 can be symmetrical or asymmetrical relative to one another about the mid-longitudinal axis L, and the asymmetry can be used to accommodate patients with different ailments, injuries, and/or deformities.

Figure 6:
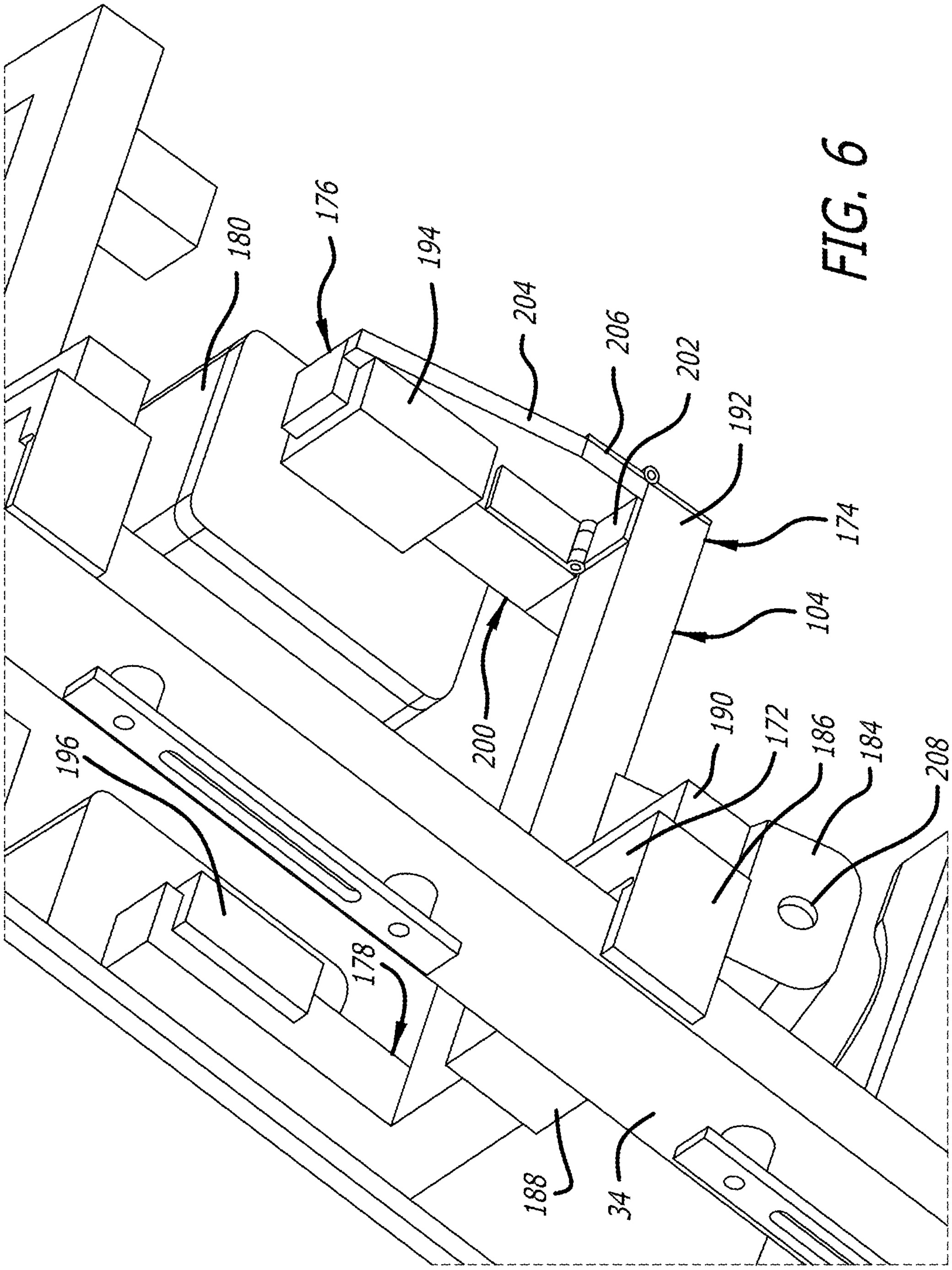
FIG. 6 is an enlarged, bottom, second side, perspective view of a first portion of the first embodiment of the frame and patient support of FIG. 1.
Figure 7:
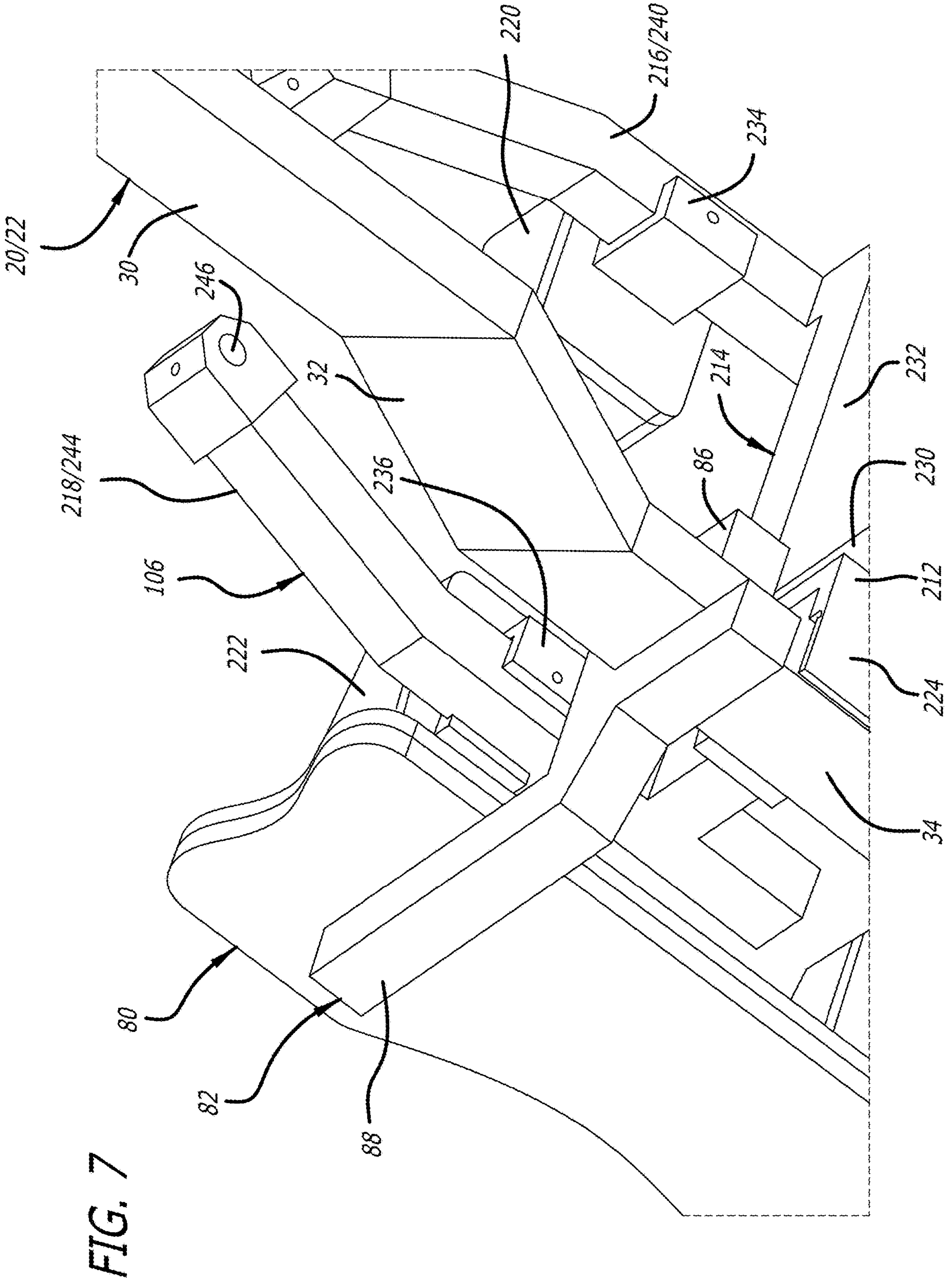
FIG. 7 is an enlarged, bottom, second side, perspective view of a second portion of the first embodiment of the frame and patient support of FIG. 1.

Additionally, a hinged portion 200 of the first arm portion 176 can be pivoted downwardly from an upward position to move the first pad portion 180 away from the patient and out of the surgeon's way to provide additional access to the left lateral side thereof. To illustrate, as depicted in FIG. 6, the hinged portion 200 of the first arm portion 176 can support the first pad portion 180, and can be hingedly attached to the second portion 192 of the base portion 174 using a first hinge 202 that affords downward pivotal movement of the hinged portion 200 from the upward position. Additionally, a support portion 204 can be pivoted into and out of position to support the hinged portion 200 in the upward portion. The support portion 204 can be hingedly attached to the second portion 192 of the base portion 174 using a second hinge 206 that affords pivotal movement thereof. Thus, when the patient is supported in the prone position on the frame and patient support 10, the support portion 204 can be pivoted out of position relative to the hinged portion 200, and the hinged portion 200 can be pivoted downwardly from the upward position to break the first pad portion 180 away from the left lateral side of the patient to provide additional access thereto. To provide yet additional access to the left lateral side of the patient, the first pad portion 180 can be removed from the hinged portion 200 by slidably removing the first slidable member 194 therefrom.

Figure 23:
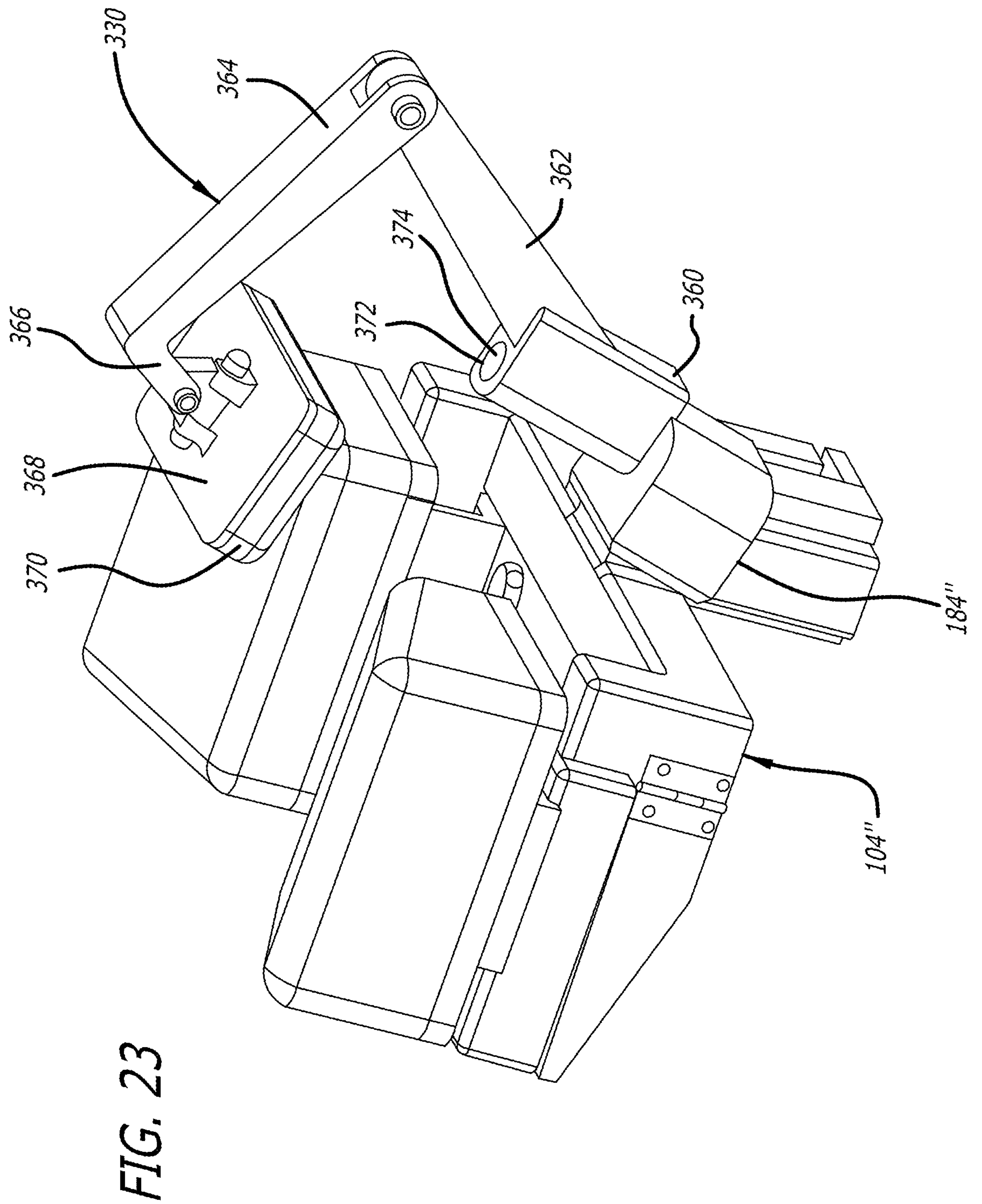
FIG. 23 is a top, first side, second end, perspective view of a pelvic-support of the frame and patient support of FIG. 21.

To secure attachment of the patient's pelvic area to the pelvic-support 104, the extension portion 184 can be used to support a pelvic hold-down portion such as that disclosed in U.S. Ser. No. 18/238,289, which is hereby incorporated by reference herein, or, as depicted in FIG. 23, a pelvic-hold-down portion 330. As depicted in FIG. 14C, the extension portion 184 extends outwardly from the base portion 174, and portions of the pelvic hold-down portion from U.S. Ser. No. 18/238,289 or the pelvic-hold-down portion 330 can be received in an aperture 208 formed in the extension portion 184. The portions of the pelvic hold-down portion can be supported by adjusted relative to the aperture 208. When engaged to the patient's pelvic area, the pelvic hold-down portion can clamp the patient's pelvic area to the first pad portion 180 and the second pad portion 182.

Figure 14D:
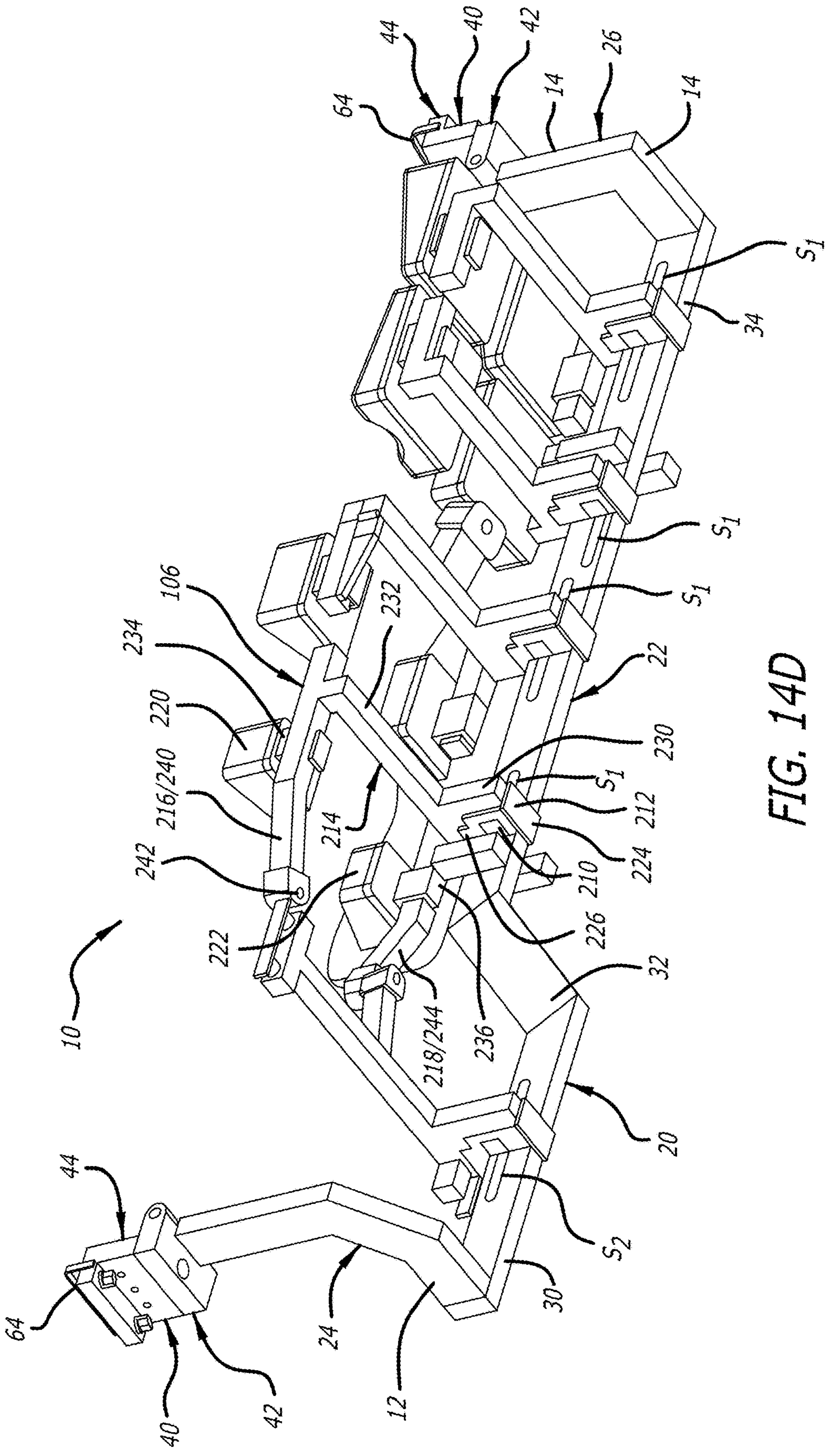
FIG. 14D is a bottom, first side, first end, perspective view of the first embodiment of the frame and patient support of FIG. 1 similar to FIGS. 14A-14C.

The torso-support 106 can be used to support at least portions of the patient's torso or torso area, and, as depicted in FIG. 14D, for example, includes a first bracket portion 210, a second bracket portion 212, a base portion 214, a first arm portion 216, a second arm portion 218, a first pad portion 220, a second pad portion 222. A first portion of the first bracket portion 210 can be received in a complimentary-shaped structure within a fourth portion of the interior of the third portion 34 and extends through one of the slots S1, and using, for example, a slide bearing having bushing and carriage, is slidably moveable with respect to the third portion 34. The interaction of the first bracket portion 210 within the interior of the third portion 34 serves to counteract moments of inertia caused by the supporting of the portion of the patient's torso or torso area by the torso-support 106. A second portion of the first bracket portion 210 is attached to the first portion thereof and is moveable on the exterior of the third portion 34, and the second bracket portion 212 can be attached to the second portion of the first bracket portion 210. The second bracket portion 212 can be used to secure attachment of the first bracket portion 210 (and remaining portions of the torso-support 106) to the third portion 34 in a selected location via receipt of one or more fasteners (not shown) through a first engagement tongue 224 thereof to contact a lower portion of the third portion 34, and/or a second engagement tongue 226 thereof to contact an upper portion of the third portion 34.

The second bracket portion 212 is attached to the first bracket portion 210, and, as depicted in FIG. 14D, supports the base portion 214 relative to the first bracket portion 210. The base portion 214 can be fixedly or pivotally attached relative to the second bracket portion 212. The base portion 214 can include a first portion 230 that can be oriented vertically, and a second portion 232 that can be oriented horizontally. The first portion 230 of the base portion 214 can be fixedly or pivotally attached relative to the second bracket portion 212, and the second portion 232 of the base portion 214 can effectively extend outwardly from the third portion 34. The second portion 232 of the base portion 214 can support each of the first arm portion 216 and the second arm portion 218 at opposite ends thereof, and portions of the first arm portion 216 and the second arm portion 218 can extend from the second portion 232 toward the first end 12 and the second end 14. While the first arm portion 216 and the second arm portion 218 are shown as being aligned with the mid-longitudinal axis L, the first arm portion 216 and the second arm portion 218 can alternatively be angled inwardly or outwardly and/or upwardly or downwardly relative to the mid-longitudinal axis L. These angles of the first arm portion 216 and the second arm portion 218 can be fixed or variable (via adjustable attachment thereof to the second portion 232) can be used to position the first pad portion 220 and the second pad portion 222 to accommodate different types of surgeries, as well as differently sized patients and/or patients having ailments, injuries, and/or deformities.

The first pad portion 220 can support a left portion of the patient's torso or torso area, and can be moveably supported relative to the first arm portion 216 using a first slidable member 234 slidably moveable along a portion of the first arm portion 216; and the second pad portion 222 can support a right portion of the patient's torso area, and can be moveably supported relative to the second arm portion 218 using a second slidable member 236 slidably moveable along a portion of the second arm portion 218. The first pad portion 220 and the second pad portion 222 can each include an integrated plate portion that is rotatably and/or slidably attached to a corresponding one of the first slidable member 234 and the second slidable member 236. The first pad portion 220 and the second pad portion 222 can be rotated independently of one another, slidable independently of one another inwardly and outwardly relative to one another, and slidably moved independent of one another in directions aligned or substantially aligned with the mid-longitudinal axis (via the first slidable member 234 and the second slidable member 236), and can be secured in selected locations along portions of the first arm portion 216 and the second arm portion 218, respectively, using fasteners (not shown) received therethrough and engaging the first arm portion 216 and the second arm portion 218. Furthermore, the rotational and/or slidable positions of the first pad portion 220 and the second pad portion 222 can be secured in selected rotational or slidable positions. As such, to accommodate patients having different heights, general adjustment can be provided by positioning and repositioning the location of the torso-support 106 relative to the third portion 34, and then finer adjustment can be provided by independent positioning and repositioning the locations of the first pad portion 220 and the second pad portion 222 to additionally accommodate the specific anatomy of the patient. And to accommodate patients having different ailments, injuries, and/or deformities, the orientations (slidable or rotational) of the first pad portion 220 and the second pad portion 222 can be adjusted to accommodate these ailments, injuries, and/or deformities. As such, the adjustability of the first pad portion 220 and the second pad portion 222 can be symmetrical or asymmetrical relative to one another about the mid-longitudinal axis L, and the asymmetry can be used to accommodate patients with different ailments, injuries, and/or deformities.

Figure 4:
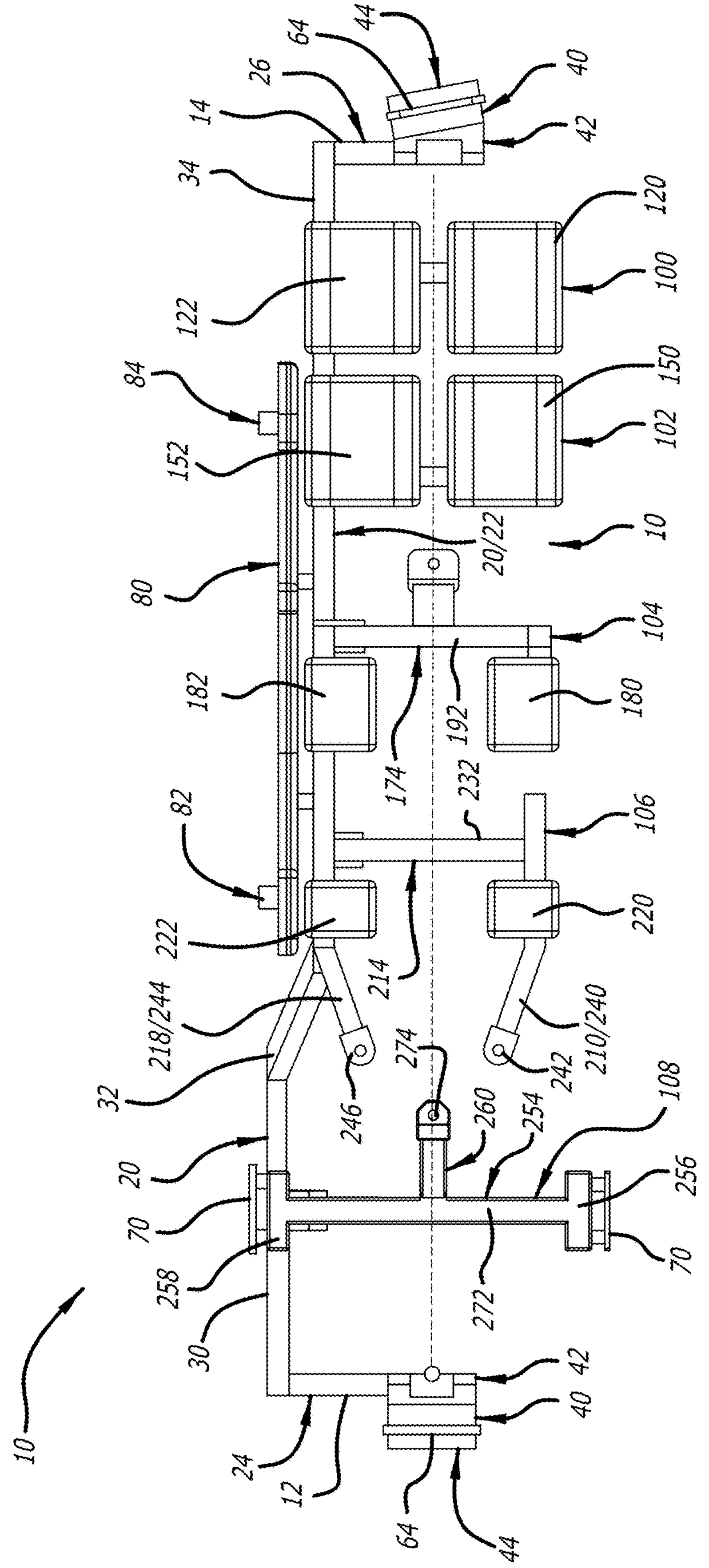
FIG. 4 is a top, plan view of the first embodiment of the frame and patient support of FIG. 1.
Figure 5:
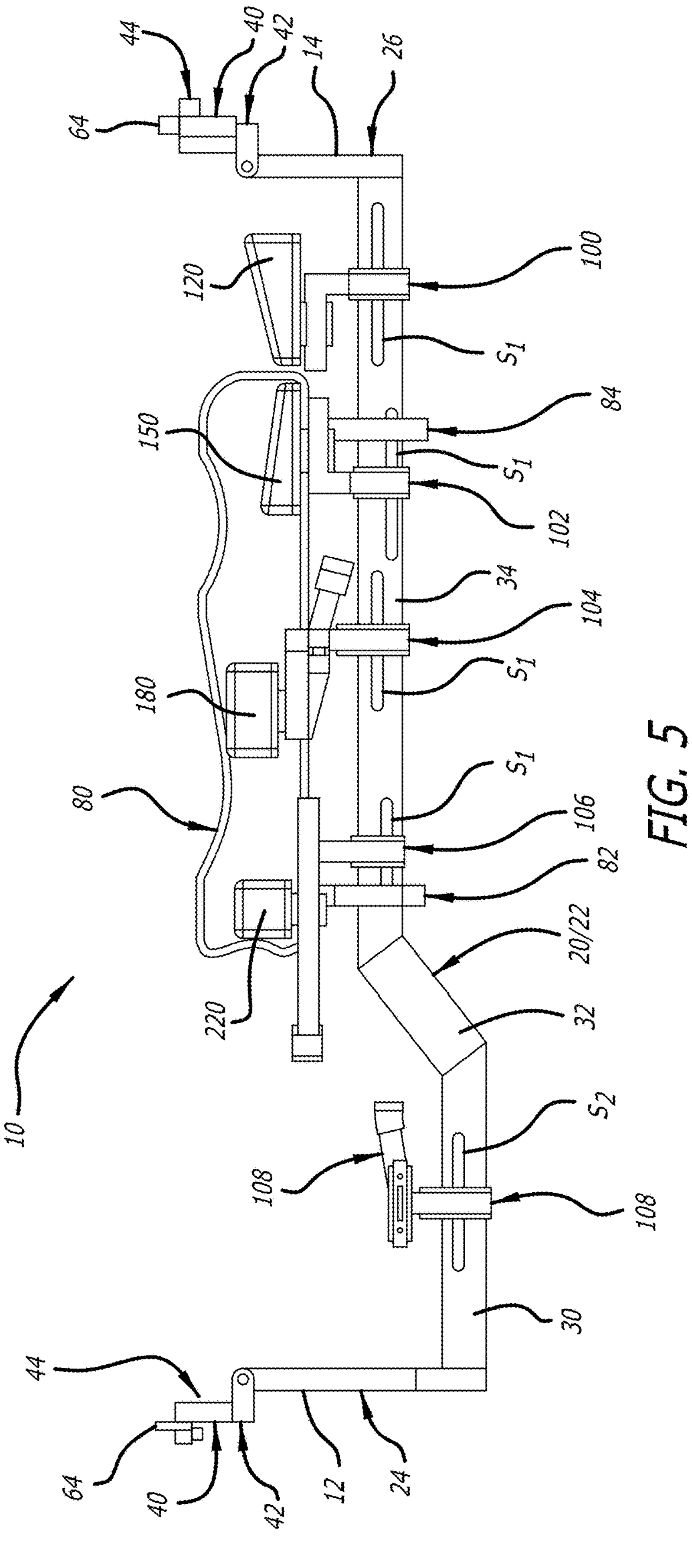
FIG. 5 is a first side, elevational view of the first embodiment of the frame and patient support of FIG. 1.
Figure 24:
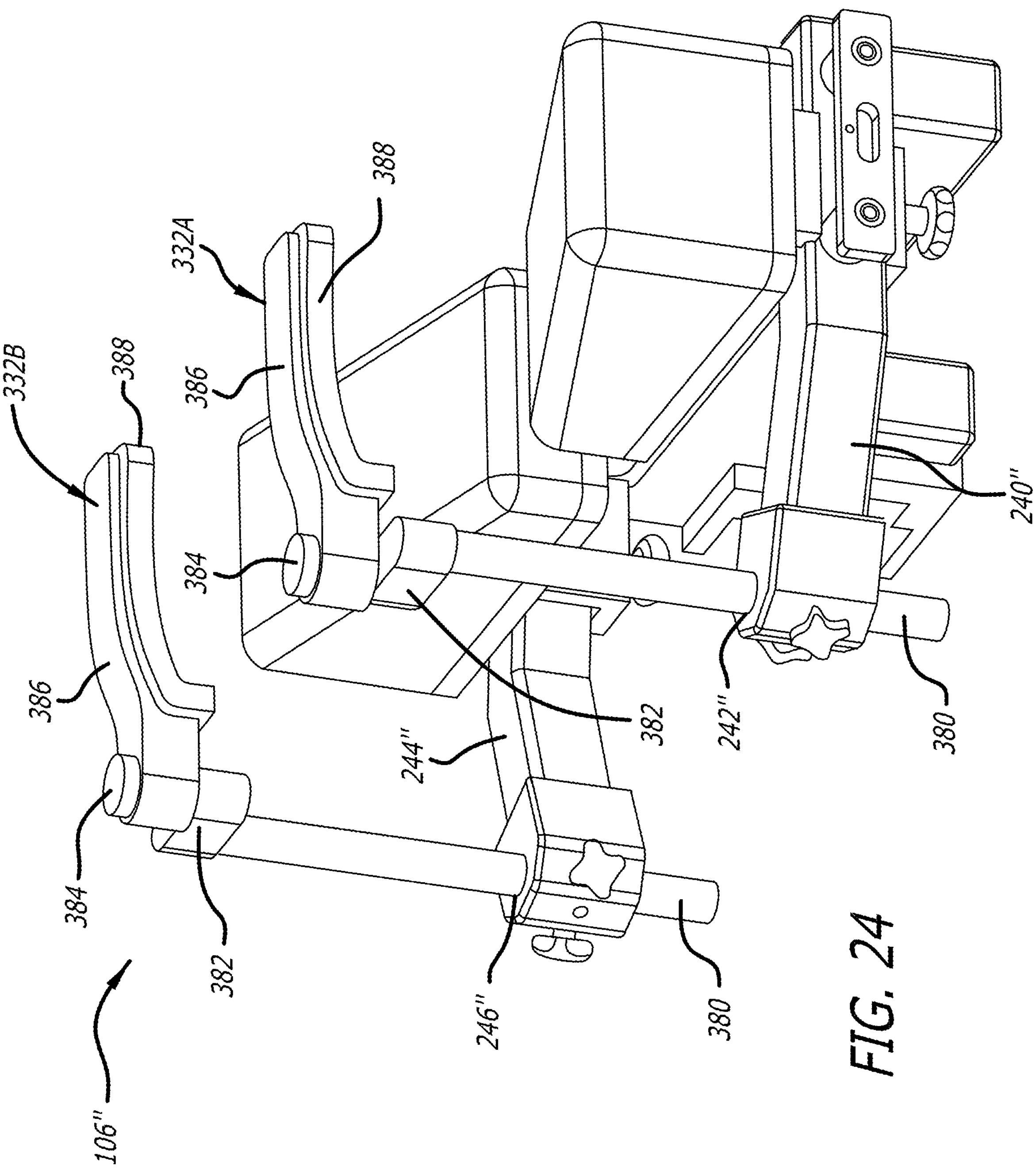
FIG. 24 is a top, first side, first end, perspective view of a torso-support of the frame and patient support of FIG. 21.

To secure attachment of the patient's torso area to the torso-support 106, each of the first arm portion 216 and the second arm portion 218 can be used to support a shoulder hold-down portions such as that also is disclosed in U.S. Ser. No. 18/238,289, or, as depicted in FIG. 24, shoulder-hold-down portions 332A and 332B. As depicted in FIG. 4, the first arm portion 216 can include a first extension portion 240 with a first aperture 242 formed therein, and the second arm portion 218 can include a second extension portion 244 with a second aperture 246 formed therein. The first extension portion 240 and the second extension portion 244 can each include an end portion that can be structurally reinforced and mechanically durable, and these end portions can be removable and/or replaceable, so that any connection apertures such as the first aperture 242 and the second aperture 246 formed therein (or other connection mechanism) can be maintained in a mechanically-sound configuration via remachining or replacement. The first extension portion 240 and the second extension portion 244 can be angled toward with one another to provide space for portions of the patient's shoulders and arms on the outside thereof. Each of the first aperture 242 and the second aperture 246 can be configured to receive portions of one of the shoulder hold-down portions from U.S. Ser. No. 18/238,289 or the shoulder-hold-down portions 332A and 332B, and the portions of these shoulder hold-down portions can be adjusted relative to the first aperture 242 and the second aperture 246. When engaged to the patient's torso area, these shoulder hold-down portions can clamp the patient's torso area to the first pad portion 220 and the second pad portion 222.

Figure 14E:
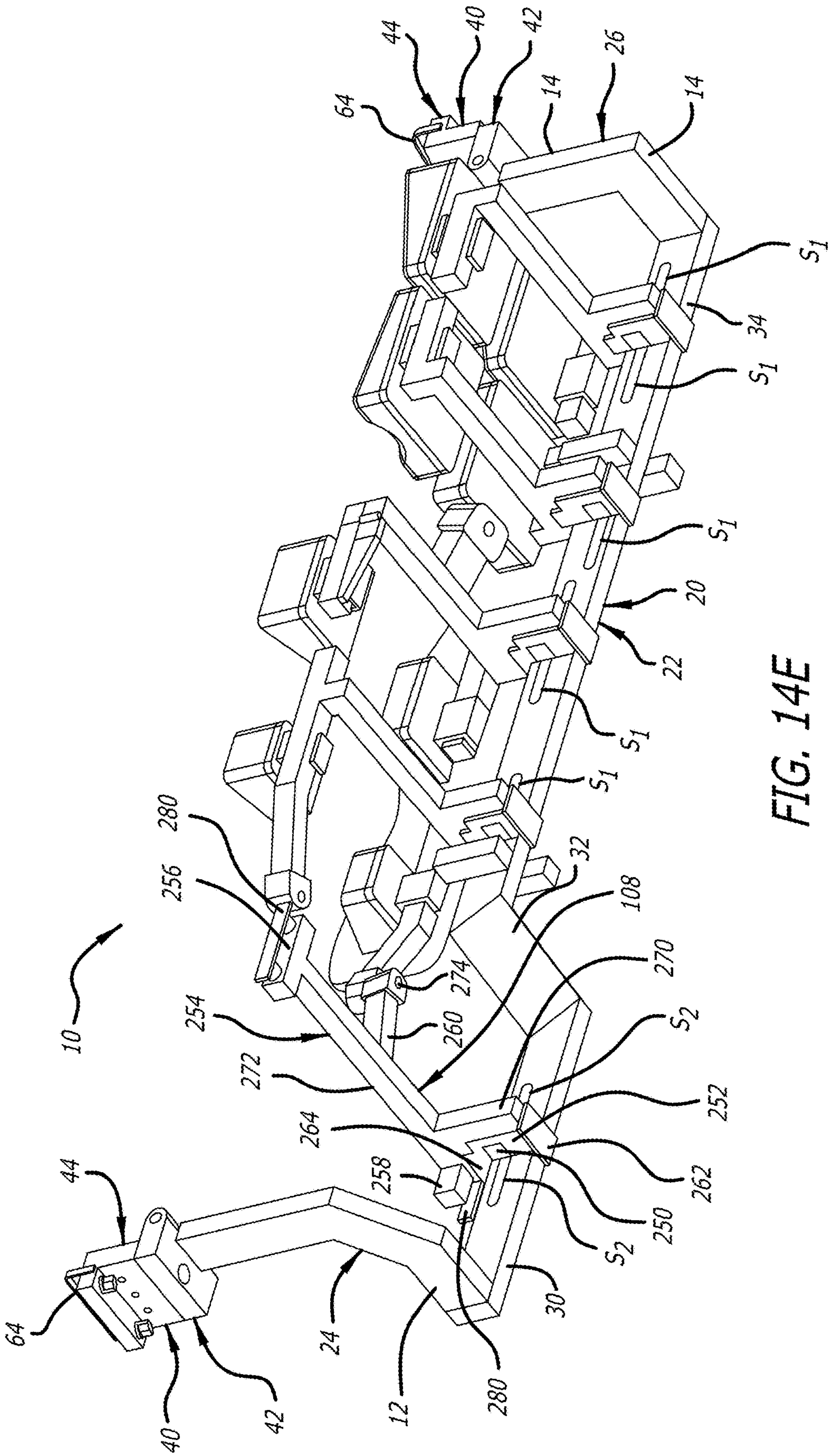
FIG. 14E is a bottom, first side, first end, perspective view of the first embodiment of the frame and patient support of FIG. 1 similar to FIGS. 14A-14D.
Figure 15:
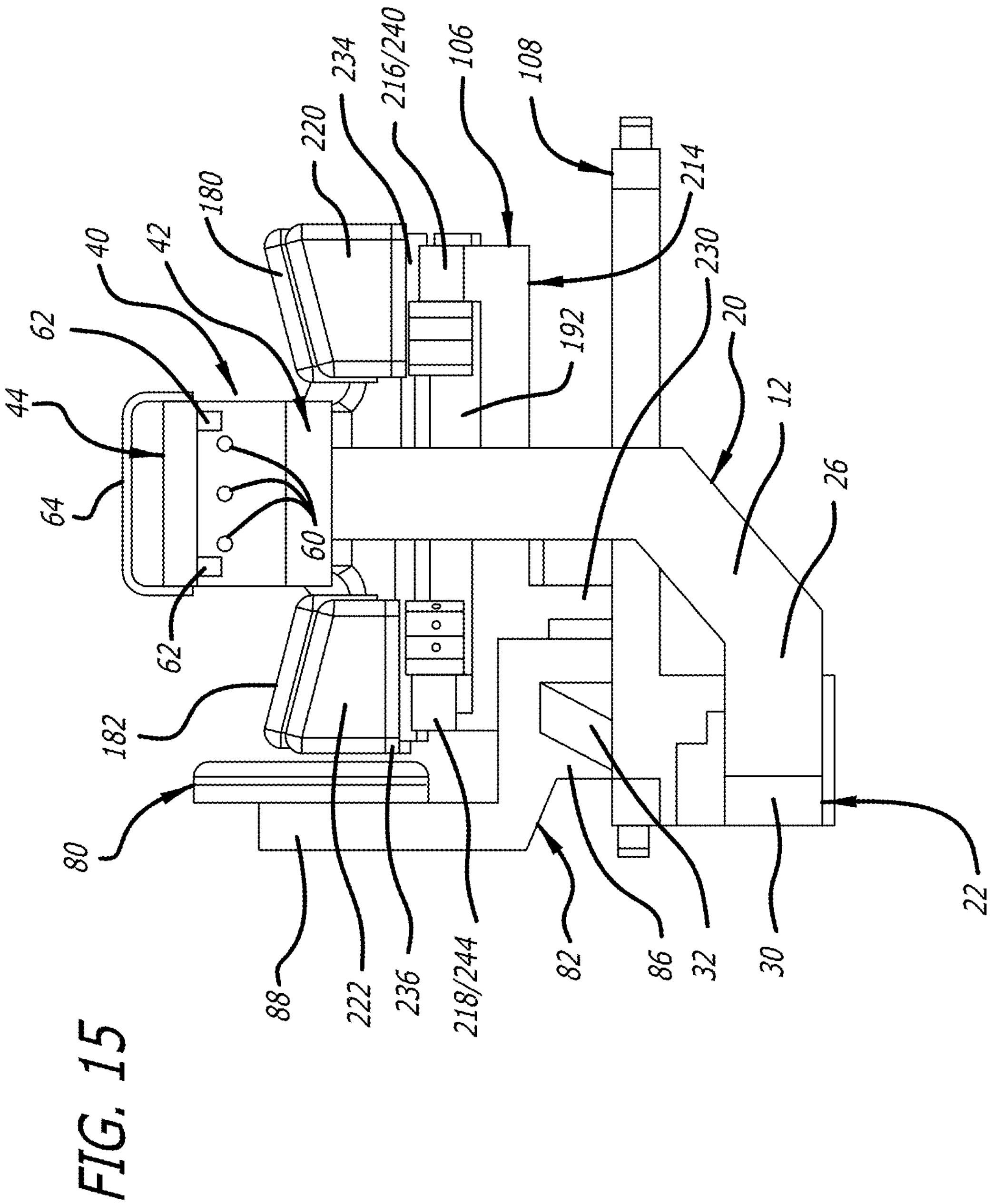
FIG. 15 is a second end, elevational view of the first embodiment of the frame and patient support of FIG. 1.

The head-and-arm-support 108 can be used to support at least portions of the patient's head and arms, and, as depicted in FIG. 14E, for example, includes a first bracket portion 250, a second bracket portion 252, a base portion 254, a first arm portion 256, a second arm portion 258, and an extension portion 260. The head-and-arm support 108 can be provided as an integrated unit attached to frame 20 to support portions of the head and the arms of the patient relative to the frame 20, or formed as separate units attached separately to the frame 20 to separately support portions of the head and arms of the patient relative to the frame 20. A first portion of the first bracket portion 240 can be received in a complimentary-shaped structure within a portion of the interior of the first portion 30 and extends through a slot S2, and using, for example, a slide bearing having bushing and carriage, is slidably moveable with respect to the first portion 30. The interaction of the first bracket portion 250 within the interior of the first portion 30 serves to counteract moments of inertia caused by the support of the portions of the patient's head and arms by the head-and-arm support 108. A second portion of the first bracket portion 250 is attached to the first portion thereof and is moveable on the exterior of the first portion 30, and the second bracket portion 252 can be attached to the second portion of the first bracket portion 250. The second bracket portion 252 can be used to secure attachment of the first bracket portion 250 (and remaining portions of the hear/arm-support 108) to the first portion 30 in a selected location via receipt of one or more fasteners (not shown) through a first engagement tongue 262 thereof to contact a lower portion of the first portion 30, and/or a second engagement tongue 264 thereof to contact an upper portion of the third portion 30.

Figure 22C:
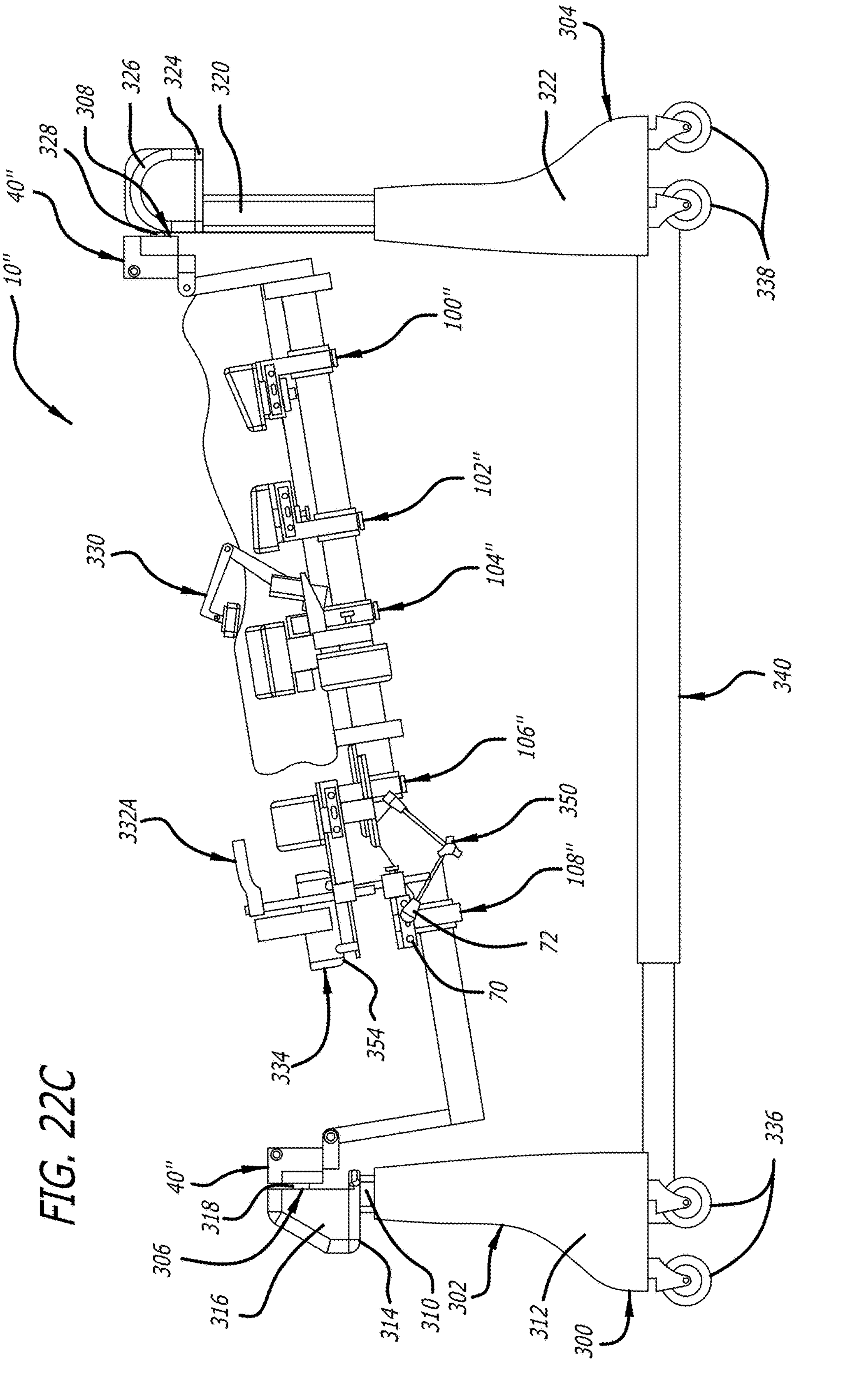
FIG. 22C is a first side, elevational view of the third embodiment of the frame and patient support of FIG. 21 supported by the frame support structure with the frame and patient support in a Trendelenburg position.
Figure 25:
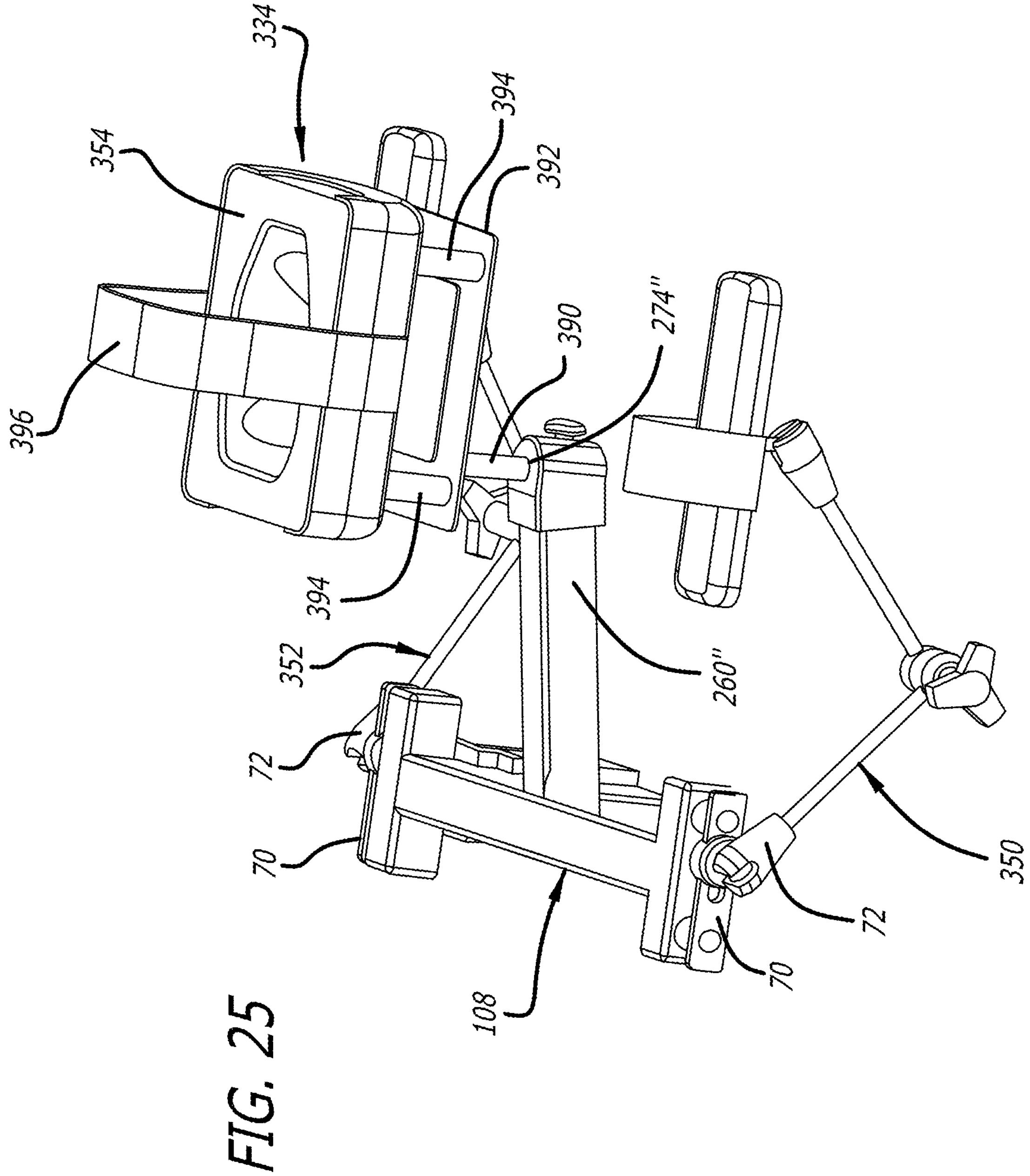
FIG. 25 is a top, first side, second end, perspective view of a head-and-arm support of the frame and patient support of FIG. 21.

The second bracket portion 252 is attached to the first bracket portion 250, and, as depicted in FIG. 14E, supports the base portion 254 relative to the first bracket portion 250. The base portion 254 can be fixedly or pivotally attached relative to the second bracket portion 252. The base portion 254 can include a first portion 270 that can be oriented vertically, and a second portion 272 that can be oriented horizontally. The first portion 270 of the base portion 254 can be fixedly or pivotally attached relative to the second bracket portion 252, and the second portion 272 of the base portion 254 can effectively extend outwardly from the first portion 30. The second portion 272 of the base portion 254 can support each of the first arm portion 256 and the second arm portion 258 at opposite ends thereof. The first arm portion 256 and the second arm portion 258 can each include one of the rails 70 provided for receiving Clark sockets 72 (FIGS. 21 22C). The rails 70 and Clark sockets 72 can be used to support arm support portions such as that disclosed in U.S. Ser. No. 18/238,289, or, as depicted in FIG. 25, a first arm support portion 350 and a second arm support portion 352. Furthermore, the extension portion 260 extends outwardly from the base portion 254, and can include an aperture 274 formed therein. The extension portion 260 can include an end portion that can be structurally reinforced and mechanically durable, and this end portion can be removable and/or replaceable, so that any connection apertures formed therein such as the aperture 274 (or other connection mechanism) can remain mechanically sound via remachining or replacement. As depicted in FIG. 25, the aperture 274 can be configured for receiving portions of a head-support portion such as that also disclosed in U.S. Ser. No. 18/238,289, or, as depicted in FIG. 25, a head-support portion 334 including a head cradle 354. The arm support portions and the head support portion can be adjusted to accommodate patients of different sizes and/or shapes.

Additionally, the frame and patient support 10 can be modified to result in a second embodiment of the frame and patient support (FIGS. 16-20) that is generally referenced by the numeral 10'. The frame and patient support 10' is similar to the frame and patient support 10, and similar element numbering is applied to the frame and patient support 10' in FIGS. 16-20 to describe elements thereof. The frame and patient support 10' can have a truncated length in comparison to the frame and patient support 10. The truncated length can better facilitate use of a C-Arm or O-Arm imaging device. To facilitate such truncation, for example, the frame and support 10' can have a frame 20' that is shortened relative to the frame 20 in the direction of the mid-longitudinal axis L, and/or a second portion 32' of the frame 20' can be angled differently than the second portion 32 relative to a first portion 30' and a third portion 34' to decrease the length of the frame 20' in the direction of the mid-longitudinal axis L.

Figure 16:
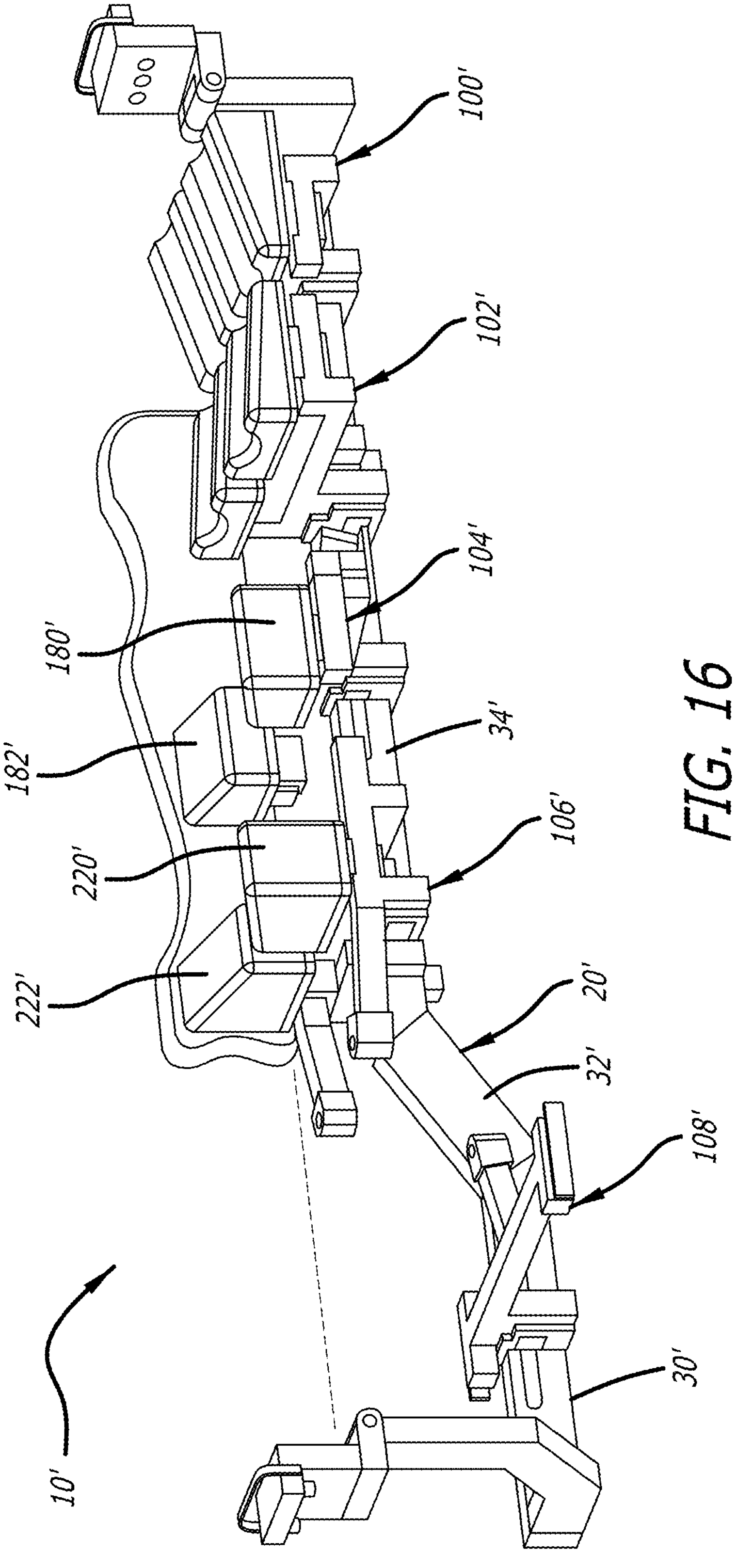
FIG. 16 is a top, first side, first end, perspective view of a second embodiment of a frame and patient support according the present disclosure.
Figure 17:
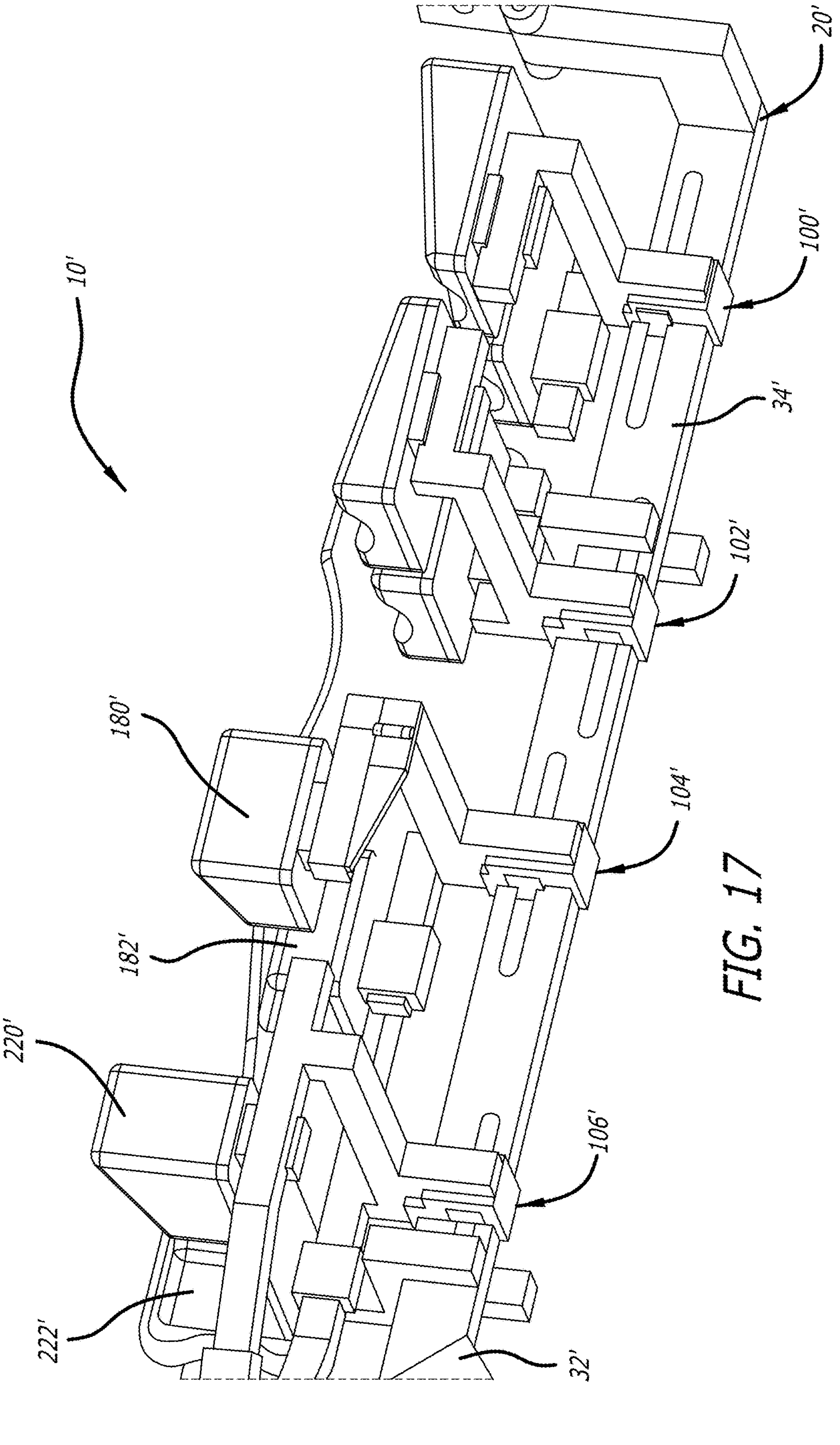
FIG. 17 is a bottom, first side, perspective view of the second embodiment of the frame and patient support of FIG. 16.
Figure 18:
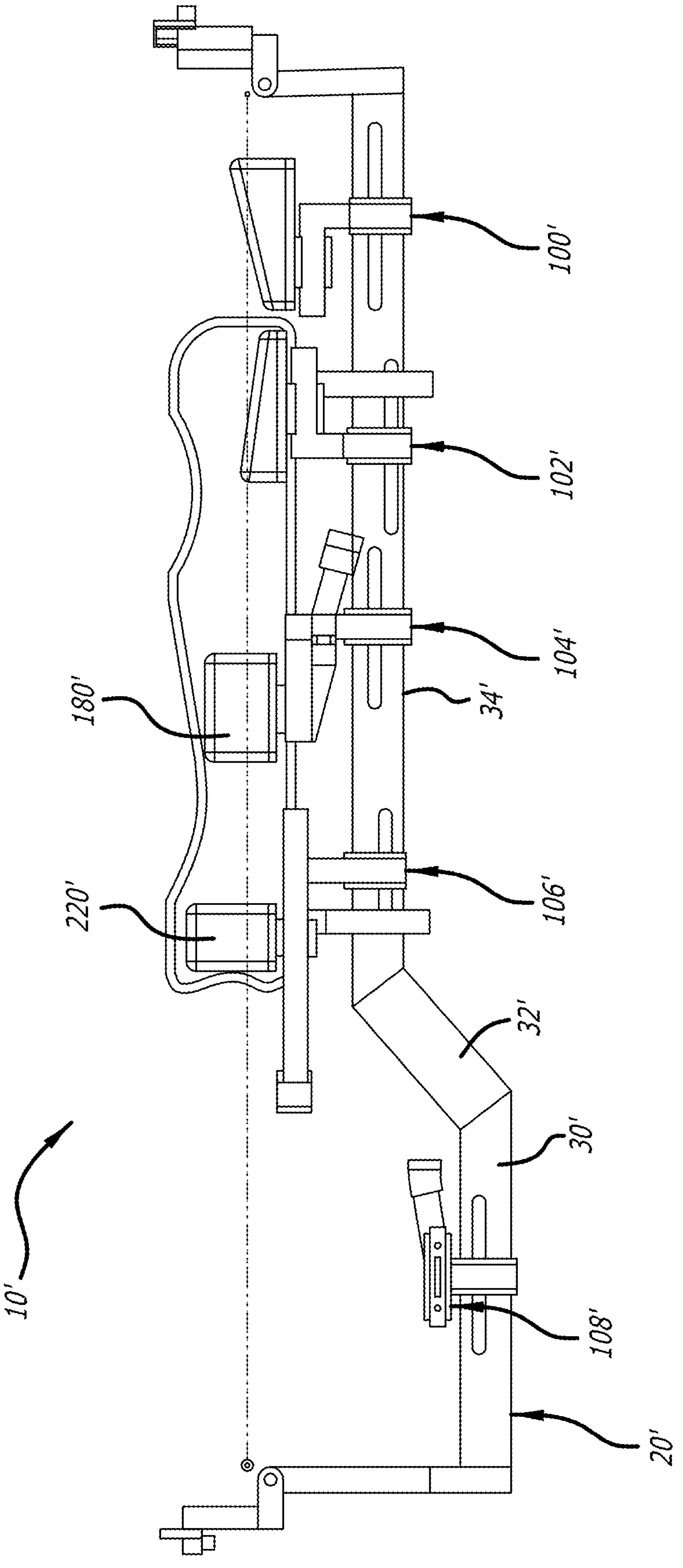
FIG. 18 is a first side, elevational view of the second embodiment of the frame and patient support of FIG. 16.
Figure 19:
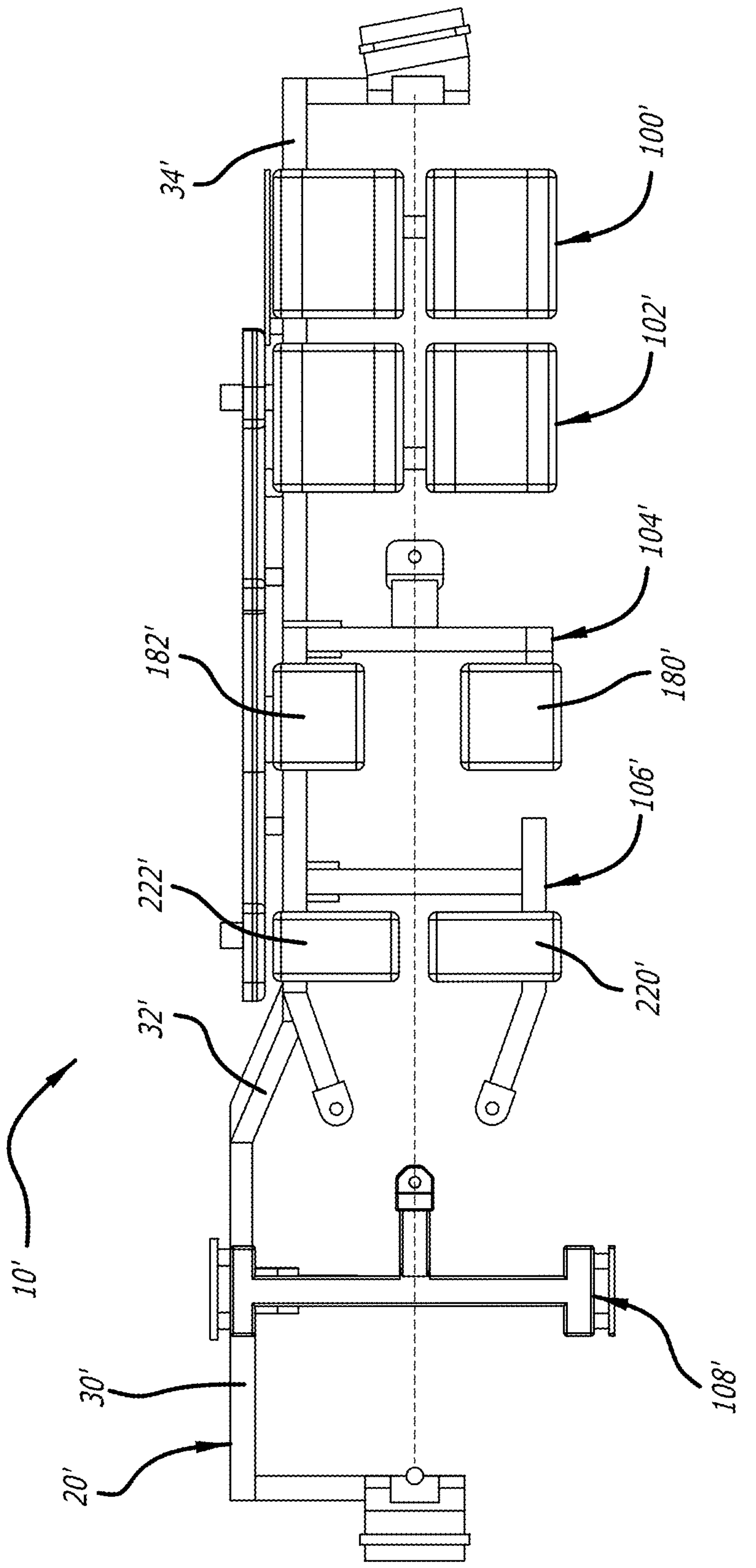
FIG. 19 is a top, plan view of the second embodiment of the frame and patient support of FIG. 16 depicting chest support pads in a first position.
Figure 20:
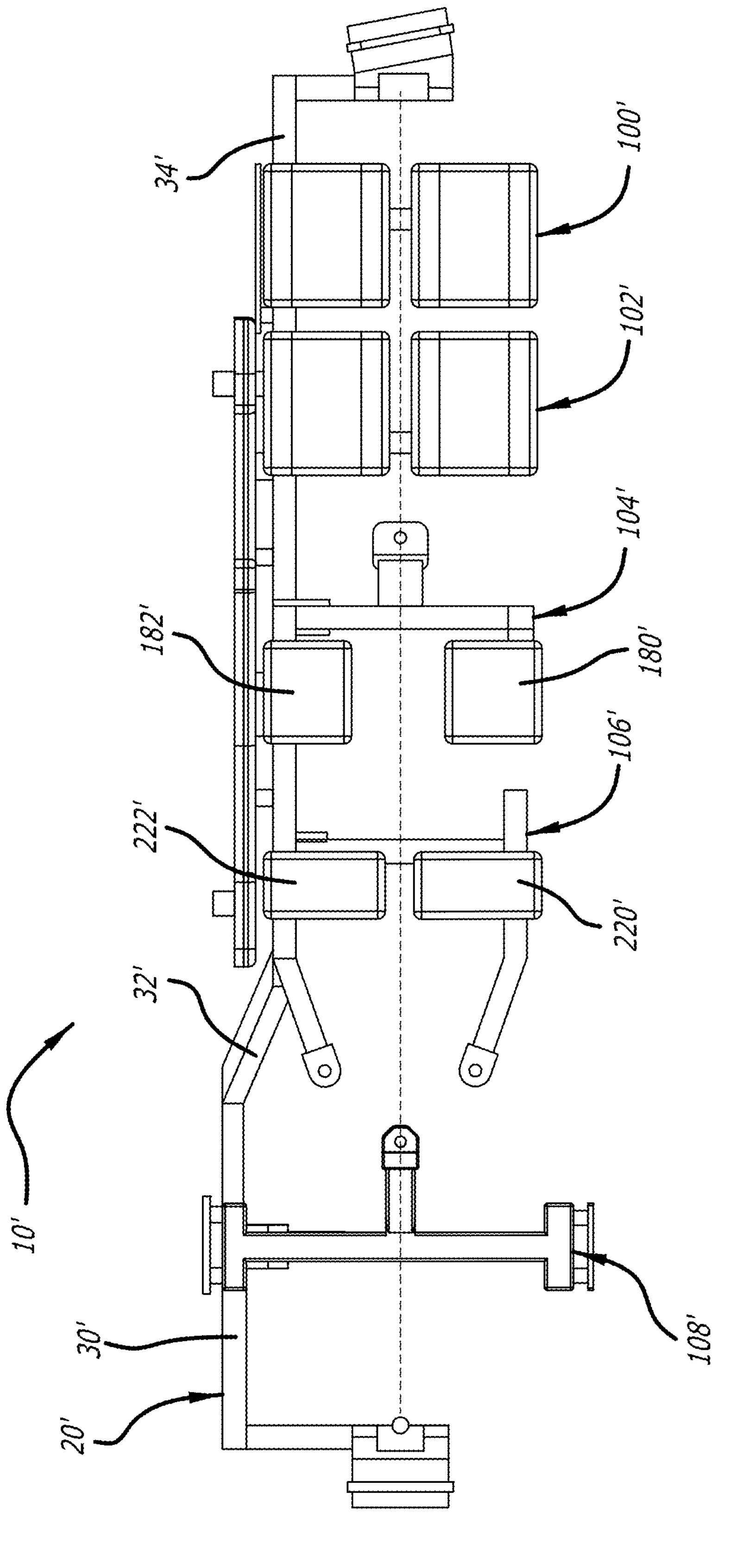
FIG. 20 is a top, plan view of the second embodiment of the frame and patient support of FIG. 16 depicting chest support pads in a second position.

The frame and patient support 10', as depicted in FIGS. 16-20, can include a lower leg support 100', an upper-leg support 102', a pelvic support 104', and a torso-support 106' that can have pads modified to have different lengths, heights (or thicknesses), and widths relative the pads of the lower-leg-support 100, the upper-leg-support 102, the pelvic-support 104, and the torso-support 106. The pads of the frame and patient support 10' can be longer or shorter, taller or shorter, and/or wider or thinner than the corresponding pads of the frame and patient support 10. For example, as depicted in FIGS. 16-18, pads 180' and 182' of the pelvic-support 104' can be taller and wider than the pads 180 and 182, and pads 220' and 222' of the torso-support 106' can be longer, taller, and wider than the pads 220 and 222. Furthermore, for example, the pads of the pelvic-support 104 and the torso-support 106 of the frame and patient support 10 can have the same or similar heights, or, as depicted in FIGS. 16-18, the heights of the pads of the pelvic-support 104' can be shorter than the pads of the torso-support 106' of the frame and patient support 10'. In addition, the pads 220' and 222' of the torso-support 106' can be modified to contact additional chest portions and/or abdomen portions of the patient's body. When contacting the abdomen portions of the patient's body, the pads 220' and 220' of the torso-support 106' can also be moved medially (FIGS. 19 and 20) along the first arm portion 216 and the second arm portion 218 to effectuate better contact the abdomen portions of the patient's body.

In addition, the frame and patient support 10 can also be modified to result in a third embodiment of the frame and patient support (FIGS. 21-22C) that is generally referenced by the numeral 10". The frame and patient support 10" is similar to the frame and patient support 10, and similar element numbering is applied to the frame and patient support 10" in FIGS. 21-22C to describe of elements thereof. The frame and patient support 10", as depicted in FIGS. 21-22C, can include a frame 20" that supports a lower-leg-support 100", an upper-leg-support 102", a pelvic-support 104", a torso-support 106", and a head-and-arm support 108" Furthermore, as depicted in FIGS. 21-22C, a first end 12" of the frame and patient support 10" can be supported by the first vertical support portion 302, and the second end 14" of the frame and patient support 10" can be supported by the second vertical support portion 304. Interconnection attachments 40" are provided at the first end 12" and the second end 14" of the frame 20", with the interconnection attachment 40" at the first end 12" being configured to attach to a first interconnector 306 of the first vertical support portion 302, and the interconnection attachment 40" at the second end 14" being configured to attach to a second interconnector 308 of the second vertical support portion 304. The first interconnector 306 and the second interconnector 308 can include complimentary structures to facilitate docking and locking of the interconnection attachments 40" thereto to afford rotation of the frame 20". The interconnection attachments 40" provided at the first end 12" and the second end 14" of the frame and patient support structure 10" can include handles similar to handles 64, or alternatively, can include handles 64" (FIG. 21) that extend outwardly from the interconnection attachments 40".

As depicted in FIGS. 21-22C, the first vertical support portion 302 can include a first expandable vertical post 310, a first skirt 312, a first platform 314, a first rotational element (not shown), a first shroud 316, and a first rotational shaft 318. The first expandable vertical post 310 can be expanded or contacted to correspondingly raise or lower the first platform 314, the first rotational element, the first shroud 316, and the first rotational shaft 318. The first expandable vertical post 310 can support the first platform 314, the first platform 314 can support the first rotational element (not shown), and the first rotational shaft 318 can be rotated using the first rotational element. The first skirt 312 can be configured to cover the first expandable vertical post 310, and the first shroud 316 can be configured to cover the first rotational element.

The first rotational element can be a motor (or other actuator) for actuating rotation of the first rotational shaft 318 or can simply rotationally support the first rotational shaft 318. The first interconnector 306 can be attached to the first rotational shaft 318, and the first interconnector 306 can include complimentary structures (not shown) to the protrusions 62 for facilitating interconnection between the first interconnector 306 and the interconnection attachment 40" at the first end 12" of the frame and patient support 10". When the interconnection attachment 40" at the first end 12" of the frame and patient support 10" is attached to the first interconnector 306, rotation of the first rotational shaft 318 facilitates rotation of the frame and patient support 10". And when the interconnection attachment 40" at the first end 12" of the frame and patient support 10" is attached to the first interconnector 306, the expansion and contraction of the first expandable vertical post 310 can be used to correspondingly raise and lower the first end 12" of the frame and patient support 10".

Additionally, an end 50" of a first end portion 24" of the frame 20" can pivot (FIGS. 22B and 22C) with respect to the axis extending through or adjacent the connection between the interconnection attachment 40" at the first end 12" and the end 50". As discussed below, such pivoting (along with expansion or contraction of the first expandable vertical post 310 and/or the second expandable vertical post 320) can afford orienting the frame 20" to position the patient, for example, in a prone position, a supine position, a lateral position, an anterolateral position, a posterolateral position, a prone reverse Trendelenburg position (FIG. 22B), a supine reverse Trendelenburg position, a prone Trendelenburg position (FIG. 22C), a supine Trendelenburg position. To avoid binding of portions of the frame and patient support 10" during such pivoting of the frame, a linear translator (not shown) can be provided between the first expandable vertical post 310 and the first platform 314 to move the first platform 314 toward and away from the first end 12", and/or the first rotational shaft 318 can be configured to be moveable inwardly and outwardly relative to the first rotational element and/or the first shroud 316.

As depicted in FIGS. 21-22C, the second vertical support portion 304 can include a second expandable vertical post 320, a second skirt 322, a second platform 324, a second rotational element (not shown), a second shroud 326, and a second rotational shaft 328. The second expandable vertical post 320 can be expanded or contacted to correspondingly raise or lower the second platform 324, the first rotational element, the first shroud 326, and the second rotational shaft 328. The second expandable vertical post 32—can support the second platform 324, the second platform 324 can support the second rotational element (not shown), and the second rotational shaft 328 can be rotated using the second rotational element. The second skirt 322 can be configured to cover the second expandable vertical post 320, and the second shroud 326 can be configured to cover the second rotational element.

The second rotational element can be a motor (or other actuator) for actuating rotation of the second rotational shaft 328 or can simply rotationally support the second rotational shaft 320. The second interconnector 308 can be attached to the second rotational shaft 328, and the second interconnector 308 can include complimentary structures (not shown) to the protrusions 62 for facilitating interconnection between the second interconnector 308 and the interconnection attachment 40" at the second end 14" of the frame and patient support 10". When the interconnection attachment 40" at the second end 14" of the frame and patient support 10" is attached to the second interconnector 308, rotation of the second rotational shaft 328 facilitates rotation of the frame and patient support 10". And when the interconnection attachment 40" at the second end 14" of the frame and patient support 10" is attached to the second interconnector 308, the expansion and contraction of the second expandable vertical post 320 can be used to correspondingly raise and lower the second end 14" of the frame and patient support 10".

Additionally, an end 52" of a second end portion 24" of the frame 20" can pivot (FIGS. 22B and 22C) with respect to the axis extending through or adjacent the connection between the interconnection attachment 40" at the second end 14" and the end 52". As discussed below, such pivoting (along with expansion or contraction of the first expandable vertical post 310 and/or the second expandable vertical post 320) can afford orienting the frame 20" to position the patient in a prone position, lateral position, anterolateral position, reverse Trendelenburg position (FIG. 22B) or a prone Trendelenburg position (FIG. 22C). To avoid binding of portions of the frame and patient support 10" during such pivoting of the frame, a linear translator (not shown) can be provided between the second expandable vertical post 320 and the second platform 324 to move the second platform 324 toward and away from the second end 14", and/or the second rotational shaft 328 can be configured to be moveable inwardly and outwardly relative to the second rotational element and/or the second shroud 326.

The angled orientation of the frame 20" afforded by the above pivoting thereof can be selected to accommodate different types of surgeries, as well as differently sized patients and/or patients having ailments, injuries, and/or deformities. Furthermore, potential pivotal angles of the frame 20" can be increased by lengthening the first rotational shaft 318 and/or the second rotational shaft 328, and/or providing additional clearance from the frame 20" to afford steeper pivoting of the frame 20".

The first vertical support portion 302 and the second vertical support portion 304 can each include a support platform (not shown), and the support platforms can serve as bases for attachment of the first expandable vertical post 320 and the second expandable vertical post 322. The support platforms can be concealed within the first skirt 312 and the second skirt 322. First casters 336 can be attached to the support platform and/or the first expandable vertical post 310 of the first vertical support portion 302, and second casters 338 can be attached to the support platform and/or the second expandable vertical post 320 of the second vertical support portion 304. And an expandable and contractable lower beam 340 can be attached between the support platform and/or the first expandable vertical post 310 of the first vertical support portion 302, and the support platform and/or the second expandable vertical post 320 of the second vertical support portion 304. The lower beam 340 can be expanded and contracted to accommodate pivoting of the frame and patient support 20" and use of the linear translator provided between the first expandable vertical post 210 and the first platform 314, the linear translator provided between the second expandable vertical post 320 and the second platform 324, the inward and outward movement of the first rotational shaft 318, and/or the inward and outward movement of the second rotational shaft 328.

FIG. 23 depicts the pelvic-support 104" of the frame and patient support 10". The pelvic-support 104" is similar to the pelvic-support 104 and the pelvic-support 104', and the pelvic-support 104" includes the pelvic hold-down portion 330 that can also be included with the pelvic-support 104 and the pelvic-support 104'. The pelvic hold-down portion 330 can include a base portion 360, a first leg portion 362, a second leg portion 364, a third leg portion 366, a plate portion 368, and a pad portion 370. The base portion 360 can be rotatably pinned to an extension portion 184'" using a pin 372 inserted through an aperture 374 provided in the base portion 360, and an aperture 208" provided in the extension portion 184". The first leg portion 362 can be pivotally attached to the base portion 360, the second leg portion 364 can be pivotally attached to the first leg portion 362, the third leg portion 366 can be attached to the second leg portion 364, the plate portion 368 can be pivotally attached to the third leg portion 366, and the plate portion 368 can support the pad portion 370. Using these rotatable and pivotal attachments, the pad portion 370 can be positioned and repositioned to contact a buttocks portion and/or a lower-back portion of the patient to secure the patient relative to the pelvic support 104". As such, using the pelvic hold-down portion 330, the patient's pelvic area can be clamped in position relative to the pelvic-support 104", and in doing so, the patient's pelvic area can be secured thereto to facilitate rotation of the frame 20" (and the patient supported thereby) relative to the first vertical support portion 302 and the second vertical support portion 304. The pad portion 370 be similarly positioned and repositioned and the patient's pelvic area can be similarly clamped in position when the pelvic hold-down portion 330 is included with the pelvic-support 104 and the pelvic-support 104'.

FIG. 24 depicts the torso-support 106" of the frame and patient support 10". The torso-support 106" is similar to the torso-support 106 and the torso-support 106', and the torso-support 106" includes the shoulder hold-down portions 332A and 332B that can also be included with the torso-support 106 and the torso-support 106'. The shoulder hold-down portions 332A and 332B are mirror images of one another, and each can include a post portion 380, an intermediate portion 382, a pin portion 384, an extension portion 386, and a pad portion 388. The post portions 380 can be slidably and rotatably received in apertures 242" and 246" of a first extension portion 240" and a second extension portion 244", respectively, the intermediate portion 382 can be pivotally attached to the post portions 380, the pin portion 384 can be attached to the intermediate portion 382, the extension portion 386 can be rotatably attached to the pin portion 384, and the extension portion 240 can support the pad portion 388. Such attachment of the intermediate portion 382 can provide eccentric positional adjustment of the pad portions 388. Using these slidable, rotatable, and pivotal attachments, the pad portions 388 can be positioned and repositioned to contact shoulder portions and/or upper-back portions of the patient to secure the patient relative the torso-portion 106". As such, using the shoulder hold-down portions 332A and 332B, the patient's torso area can be clamped in position relative to the torso-support 106", and in doing so, the patient's torso area can be secured thereto to facilitate rotation of the frame 20" (and the patient supported thereby) relative to the first vertical support portion 302 and the second vertical support portion 304. The pad portions 388 can be similarly positioned and repositioned and the patient's torso area can be similarly clamped in position when the shoulder hold-down portions 332A and 332B are included with the torso-support 106 and the torso-support 106'. The shoulder hold-down portions 332A and 332B and the pelvic hold-down portion 330 are separate from another and afford independent clamping of the patient's torso area and the patient's pelvic area.

FIG. 25 depicts the head-and-arm support 108" of the frame and patient support 10". The head-and-arm support 108" is similar to the head-and-arm support 108 and the head-and-arm support 108', and the head-and-arm support 108" includes the first arm support portion 350, the second arm support portion 352, and the head support portion 334 includes the head cradle 354 that can also be included with the head-and-arm-support 108 and the head-and-arm-support 108'. The first arm support portion 350 and the second arm support portion 352 can be adjusted into position to support a left arm portion and a right arm portion, respectively, of the patient, and the head cradle 354 can be adjusted into position to support the head of the patient. The head support portion 334 includes a post portion 390, a plate portion 392, a mirror incorporated as part of or mounted onto plate portion 392 (under the head cradle 354), posts 394, and a strap 396. The post portion 390 supports the plate portion 392, the posts 394 support the head cradle 354 relative to the plate portion 392, and the strap 396 secures the head of the patient relative to the head cradle 354. The post portion 390 can be slidably and rotatably received in an aperture 274" of an extension portion 260".

Using the frame and patient supports 10, 10', and 10", the patient can be supported and manipulated before, during, and after surgery, During such manipulation, the patient can be rotated relative to the first vertical support portion 302 and the second vertical support portion 304, and portions of the patient can be adjusted to accommodate patients of different heights, and positioned and repositioned before, during, and after surgery using the lower-leg-support 100, the upper-leg-support 102, the pelvic-support 104, the torso-support 106, and the head-and-arm-support 108, and the corresponding analogs of the frame and patient support 10' and 10". The clamping action afforded by use of the pelvic hold-down portion 330 and the shoulder hold-down portions 332A and 332B can afford such rotation. And, the lower-leg-support 100, the upper-leg-support 102, the pelvic-support 104, the torso-support 106, the head-and-arm-support 108, and the analogs thereof can be generally and finely adjusted as discussed above.

To illustrate, the lower-leg-support 100 can be generally adjusted via movement relative to one of the slots $S_1$ formed in the third portion 34 of the frame 20, and the first pad portion 120 and the second pad portion 122 can be finely adjusted via movement thereof relative to the first arm portion 116 and the second arm portion 118, respectively. The upper-leg-support 102 can be generally adjusted via movement relative to one of the slots $S_1$ formed in the third portion 34 of the frame 20, and the first pad portion 150 and the second pad portion 122 can be finely adjusted via movement thereof relative to the first arm portion 146 and the second arm portion 148, respectively. The pelvic-support 104 can be generally adjusted via movement relative to one of the slots $S_1$ formed in the third portion 34 of the frame 20, and the first pad portion 180 and the second pad portion 182 can be finely adjusted via movement thereof relative to the first arm portion 176 and the second arm portion 178, respectively. The torso-support 106 can be generally adjusted via movement relative to one of the slots $S_1$ formed in the third portion 34 of the frame 20, and the first pad portion 220 and the second pad portion 222 can be finely adjusted via movement thereof relative to the first arm portion 216 and the second arm portion 218, respectively. The head-and-arm-support 108 can be generally adjusted via movement relative to the slot $S_2$ formed in the first portion 30 of the frame 20, and the first arm support portion 350 and the second arm support portion 352 can be finely adjusted via movement relative to the first arm portion 256 and the second arm portion 258, respectively, and the head support 334 can be finely adjusted relative to the extension portion 260. The analogs of the lower-leg-support 100, the upper-leg-support 102, the pelvic-support 104, the torso-support 106, and the head-and-arm-support 108 of the frame and patient support 10' and the frame and patient support 10" can be similarly adjusted. As such, the lower-leg-support 100, the upper-leg-support 102, the pelvic-support 104, the torso-support 106, and the head-and-arm-support 108 can be moved independently of one another along the corresponding slots $S_1$ and $S_2$. Furthermore, the independent adjustment of the pelvic-support 104 and the torso-support 106 (along with the adjustment of the corresponding pad portions thereof) can also afford translation, distraction, compression, rotation, twisting, bending, and/or flexing of the patient's spine. And the clamping of the patient's pelvic area to the pelvic-support 104 and the clamping of the patient's torso to the torso-support 106 can aid in such translation, distraction, compression, rotation, twisting, bending, and/or flexing of the patient's spine. The independent adjustment of the pelvic-support 104 and the torso-support 106 along the frame 20, the adjustment of the corresponding pad portions, and the rotation of the frame 20 can be used, for example, in affording distraction, compression, and translation of the patient's thorax in relation to extension and rotation of the patient's pelvis. As such, the frame and patient supports 10, 10', and 10" can afford improved access to and manipulation of the patient's spine to correspondingly facilitate improve patient-health outcomes resulting from spinal surgery.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (for example, all described acts or events may not be necessary to carry out the techniques). In addition, while certain aspects of this disclosure are described as being performed by a single module or unit for purposes of clarity, it should be understood that the techniques of this disclosure may be performed by a combination of units or modules.

The invention claimed is:

1. A method of utilizing a frame and patient support to support portions of a body of a patient, the method comprising:

- providing the frame and patient support, the frame and patient support including a frame portion having a first end, an opposite second end, a mid-longitudinal axis extending through the first end and the second end, and a length along the mid-longitudinal axis between the first end and the second end, and a plurality of patient support portions attached to the frame portion;
- supporting portions of a pelvic area of the patient with a pelvic-support portion of the patient support portions moveably attached to the frame portion, the pelvic-support portion including at least one bracket support portion, a first arm portion, and a second arm portion, the at least one bracket support portion including a free end portion and an opposite attachment portion moveably attached to the frame portion, the free end portion spaced apart from the frame portion, and the attachment portion being repositionable between a first position and a second position along the length of the frame portion, the first arm portion extending outwardly from and being moveably attached to the at least one bracket support portion adjacent to the free end portion, and the first arm portion being moveable between a first engaged position and a second disengaged position, and the second arm portion extending outwardly from and continues being attached to the at least one bracket support portion adjacent to the frame portion;

adjusting, when the first arm portion is in the first engaged position, a position of a first pad portion along the first arm portion to support a first lateral portion of the pelvic area of the patient, and adjusting a position of a second pad portion along the second arm portion to support an opposite second lateral portion of the pelvic area of the patient;

when the first arm portion is in the first engaged position, supporting the first arm portion with a support portion pivotally attached to the at least one bracket support portion adjacent to the free end portion; and after the first pad portion and the second pad portion are positioned to support a corresponding one of the first lateral portion and the second lateral portion of the pelvic area of the patient, moving the first arm portion of the pelvic-support portion from the first engaged position to the second disengaged position to move the first pad portion away from the first lateral portion of the pelvic area to provide access to the first lateral portion of the patient by pivoting the support portion away from the first arm portion to remove support of the first arm portion provided by the support portion.

2. The method of claim 1, wherein the first arm portion is pivotally attached to the at least one bracket support portion.

3. The method of claim 1, wherein the pelvic-support portion is moveable along the frame portion via movement of the attachment portion between the first position and the second position with the first position being closer to the first end than the second position.

4. The method of claim 1, further comprising at least one of adjusting a position of the pelvic-support portion relative to the frame portion to generally accommodate the height of the patient, and the adjusting the position of the first pad portion and the position of the second pad portion serves to accommodate the specific anatomy of the patient.

5. The method of claim 4, further comprising supporting portions of a torso area of the patient with a torso-support portion of the patient support portions moveably attached to the frame portion; and supporting one of portions of a head of the patient with a head support portion of the patient support portions and portions of arms of the patient with an arm support portion of the patient support portions, at least one of the head support portion and the arm support portion being moveably attached to the frame portion.

6. The method of claim 1, wherein at least a portion of the at least one bracket support portion of the pelvic-support portion is received in an interior portion of the frame portion, and wherein interaction of the at least a portion of the at least one bracket support portion with the interior portion serves in counteracting moments of inertia caused by the supporting of the first and second portions of the pelvic area of the patient.

7. The method of claim 1, further comprising rotatably supporting the first end of the frame portion by a first vertical support portion, and rotatably supporting the second end of the frame portion by a second vertical support portion.

8. A method of utilizing a frame and patient support to support portions of a body of a patient, the method comprising:

providing the frame and patient support, the frame and patient support including a frame portion having a first end, an opposite second end, a mid-longitudinal axis extending through the first end and the second end, and a length along the mid-longitudinal axis between the first end and the second end, and a plurality of patient support portions attached to the frame portion;

supporting portions of a pelvic area of the patient with a pelvic-support portion of the patient support portions moveably attached to the frame portion, the pelvic-support portion including at least one bracket support portion, a first arm portion, and a second arm portion, the at least one bracket support portion including a free end portion and an opposite attachment portion moveably attached to the frame portion, the free end portion spaced apart from the frame portion, and the attachment portion being repositionable between a first position and a second position along the length of the frame portion the first arm portion extending outwardly from and being moveably attached to the at least one bracket support portion adjacent to the free end portion, and the first arm portion being moveable between a first engaged position and a second disengaged position, and the second arm portion extending outwardly from and continues being attached to the at least one bracket support portion adjacent to the frame portion;

adjusting, when the first arm portion in the first engaged position, a position of a first pad portion along the first arm portion to support a first lateral portion of the pelvic area of the patient, and adjusting a position of a second pad portion along the second arm portion to support an opposite second lateral portion of the pelvic area of the patient;

when the first arm portion is in the first engaged position, supporting the first arm portion with a support portion pivotally attached to the at least one bracket support portion adjacent to the free end portion; and after the first pad portion and the second pad portion are positioned to support a corresponding one of the first lateral portion and the second lateral portion of the pelvic area of the patient, pivoting the support portion away from the first arm portion to remove support from the first arm portion to allow movement of first arm portion, and moving the first arm portion of the pelvic-support portion from the first engaged position to the second disengaged position to move the first pad portion away from the first lateral portion of the pelvic area to provide access to a lateral portion of the patient.

9. The method of claim 8, wherein the first arm portion is pivotally attached to the at least one bracket support portion.

10. The method of claim 9, wherein the support portion is pivotally attached to the at least one bracket support portion.

11. The method of claim 8, wherein the pelvic-support portion is moveable along the frame portion via movement of the attachment portion between the first position and the second position with the first position being closer to the first end than the second position.

12. The method of claim 8 further comprising at least one of adjusting a position of the pelvic-support portion to the frame portion to generally accommodate the height of the patient, and wherein the adjusting the position of the first pad portion and the position of the second pad portion serves to accommodate the specific anatomy of the patient.

13. The method of claim 12, further comprising supporting portions of a torso area of the patient with a torso-support portion of the patient support portions moveably attached to the frame portion; and supporting one of portions of a head of the patient with a head support portion of the patient support portions and portions of arms of the patient with an arm support portion of the patient support portions, at least one of the head support portion and the arm support portion being moveably attached to the frame portion.

14. The method of claim 8, wherein at least a portion of the at least one bracket support portion of the pelvic-support portion is received in an interior portion of the frame portion, and interaction of the at least a portion of the at least one bracket support portion with the interior portion serves in counteracting moments of inertia caused by the supporting of the first and second portions of the pelvic area of the patient.

15. The method of claim 8, further comprising rotatably supporting the first end of the frame portion by a first vertical support portion, and rotatably supporting the second end of the frame portion by a second vertical support portion.

16. A method of utilizing a frame and patient support to support portions of a body of a patient, the method comprising:

providing the frame and patient support, the frame and patient support including a frame portion having a first end, an opposite second end, a mid-longitudinal axis extending through the first end and the second end, and a length along the mid-longitudinal axis between the first end and the second end, and a plurality of patient support portions attached to the frame portion;

supporting portions of a pelvic area of the patient with a pelvic-support portion of the patient support portions moveably attached to the frame portion, the pelvic-support portion including at least one bracket support portion, a first arm portion, and a second arm portion, the at least one bracket support portion including a free end portion and an opposite attachment portion moveably attached to the frame portion, the free end portion spaced apart from the frame portion, and the attachment portion being repositionable between a first position and a second position along the length of the frame portion, the first arm portion extending outwardly from and being pivotally attached to the at least one bracket support portion adjacent to the free end portion, and the first arm portion being pivotable between a first engaged position and a second disengaged position, and the second arm portion extending outwardly from and being attached to the at least one bracket support portion adjacent to the frame portion;

adjusting, when the first arm portion is in the first engaged position, a position of a first pad portion along the first arm portion to support a first lateral portion of the pelvic area of the patient, and adjusting a position of a second pad portion along the second arm portion to support an opposite second lateral portion of the pelvic area of the patient;

pivoting the support portion away from the first arm portion, and moving the first arm portion of the pelvic-support portion from the first engaged position to the second disengaged position to move the first pad portion away from the first lateral portion of the pelvic area to provide access to the first lateral portion of the patient.

17. The method of claim 16, wherein at least a portion of the at least one bracket support portion of the pelvic-support portion is received in an interior portion of the frame portion, and interaction of the at least a portion of the at least one bracket support portion with the interior portion serves in counteracting moments of inertia caused by the supporting of the first and second portions of the pelvic area of the patient.

18. The method of claim 16, further comprising rotatably supporting the first end of the frame portion by a first vertical support portion, and rotatably supporting the second end of the frame portion by a second vertical support portion.

* * * * *